(12) United States Patent
Choi et al.

(10) Patent No.: US 11,448,639 B2
(45) Date of Patent: *Sep. 20, 2022

(54) MASSIVELY PARALLEL DNA SEQUENCING APPARATUS

(71) Applicant: Roswell Biotechnologies, Inc., San Diego, CA (US)

(72) Inventors: Chulmin Choi, San Diego, CA (US); Sungho Jin, San Diego, CA (US); Paul W. Mola, San Diego, CA (US); Barry L. Merriman, San Diego, CA (US)

(73) Assignee: Roswell Biotechnologies, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/885,952

(22) Filed: May 28, 2020

(65) Prior Publication Data
US 2021/0109081 A1    Apr. 15, 2021

Related U.S. Application Data

(63) Continuation of application No. 16/073,706, filed as application No. PCT/US2017/015437 on Jan. 27, 2017, now Pat. No. 10,712,334.
(Continued)

(51) Int. Cl.
*G01N 27/00* (2006.01)
*G01N 33/487* (2006.01)
(Continued)

(52) U.S. Cl.
CPC ........ *G01N 33/48721* (2013.01); *H01M 4/92* (2013.01); *H01M 4/94* (2013.01);
(Continued)

(58) Field of Classification Search
USPC ................................................ 324/71.1, 347
See application file for complete search history.

(56) References Cited

U.S. PATENT DOCUMENTS

| | | |
|---|---|---|
| 4,923,586 A | 5/1990 | Katayama et al. |
| 5,082,627 A | 1/1992 | Stanbro |

(Continued)

FOREIGN PATENT DOCUMENTS

| | | |
|---|---|---|
| CN | 1795376 | 6/2006 |
| CN | 101231287 | 7/2008 |

(Continued)

OTHER PUBLICATIONS

USPTO; Requirement for Restriction dated Nov. 2, 2011 in U.S. Appl. No. 12/667,583.
(Continued)

*Primary Examiner* — Vincent Q Nguyen
(74) *Attorney, Agent, or Firm* — Spectrum IP Law Group LLC

(57) ABSTRACT

A DNA or genome sequencing structure is disclosed. The structure includes an electrode pair, each electrode having a tip-shaped end, the electrodes separated by a nanogap defined by facing tip-shaped ends; at least one conductive island deposited at or near each tip-shaped end; and a biomolecule having two ends, each end attached to the conductive islands in the electrode pair such that one biomolecule bridges over the nanogap in the electrode pair, wherein nucleotide interactions with the biomolecule provides electronic monitoring of DNA or genome sequencing without the use of a fluorescing element.

20 Claims, 24 Drawing Sheets

Related U.S. Application Data

(60) Provisional application No. 62/288,364, filed on Jan. 28, 2016.

(51) Int. Cl.
- *H01M 4/92* (2006.01)
- *H01M 4/94* (2006.01)
- *H01M 4/02* (2006.01)

(52) U.S. Cl.
CPC ........ *H01M 4/02* (2013.01); *H01M 2004/021* (2013.01); *H01M 2004/025* (2013.01)

(56) References Cited

U.S. PATENT DOCUMENTS

| | | |
|---|---|---|
| 5,194,133 A | 3/1993 | Clark et al. |
| 5,282,844 A * | 2/1994 | Stokes .................. A61N 1/0568 607/120 |
| 5,366,140 A | 11/1994 | Koskenmaki et al. |
| 5,414,588 A | 5/1995 | Barbee, Jr. |
| 5,486,449 A | 1/1996 | Honso et al. |
| 5,532,128 A | 7/1996 | Eggers et al. |
| 5,583,359 A | 12/1996 | Ng et al. |
| 5,639,507 A | 6/1997 | Galvagni et al. |
| 5,646,420 A | 7/1997 | Yamashita |
| 5,767,687 A | 6/1998 | Geist |
| 5,871,918 A | 2/1999 | Thorp et al. |
| 5,881,184 A | 3/1999 | Guidash |
| 5,965,452 A | 10/1999 | Kovacs |
| 5,982,018 A | 11/1999 | Wark |
| 6,051,380 A | 4/2000 | Sosnowski et al. |
| 6,060,023 A | 5/2000 | Maracas |
| 6,094,335 A | 7/2000 | Early |
| 6,110,354 A | 8/2000 | Saban |
| 6,123,819 A | 9/2000 | Peeters |
| 6,144,023 A | 11/2000 | Clerc |
| 6,238,927 B1 | 5/2001 | Abrams et al. |
| 6,440,662 B1 | 8/2002 | Gerwen et al. |
| 6,464,889 B1 | 10/2002 | Lee et al. |
| 6,506,564 B1 | 1/2003 | Mirkin et al. |
| 6,537,747 B1 | 3/2003 | Mills, Jr. et al. |
| 6,670,131 B2 | 12/2003 | Hashimoto |
| 6,673,533 B1 | 1/2004 | Wohlstadter et al. |
| 6,716,620 B2 | 4/2004 | Bashir et al. |
| 6,749,731 B2 | 6/2004 | Kobori |
| 6,762,050 B2 | 7/2004 | Fukushima et al. |
| 6,764,745 B1 | 7/2004 | Karasawa et al. |
| 6,790,341 B1 | 9/2004 | Saban |
| 6,824,974 B2 | 11/2004 | Pisharody et al. |
| 6,861,224 B2 | 3/2005 | Fujita et al. |
| 6,916,614 B1 | 7/2005 | Takenaka et al. |
| 6,958,216 B2 | 10/2005 | Kelley |
| 7,015,046 B2 | 3/2006 | Wohlstadter et al. |
| 7,075,428 B1 | 7/2006 | Oleynik |
| 7,169,272 B2 | 1/2007 | Fritsch et al. |
| 7,183,055 B2 | 2/2007 | Van Der Weide |
| 7,189,435 B2 | 3/2007 | Tuominen et al. |
| 7,202,480 B2 | 4/2007 | Yokoi et al. |
| 7,208,077 B1 | 4/2007 | Albers et al. |
| 7,276,206 B2 | 10/2007 | Augustine et al. |
| 7,399,585 B2 | 7/2008 | Gau |
| 7,432,120 B2 | 10/2008 | Mascolo et al. |
| 7,470,533 B2 | 12/2008 | Xu et al. |
| 7,507,320 B2 | 3/2009 | Hwang et al. |
| 7,531,120 B2 | 5/2009 | Van Rijn et al. |
| 7,579,823 B1 | 8/2009 | Ayliffe |
| 7,691,433 B2 | 4/2010 | Kronholz et al. |
| 7,785,785 B2 | 8/2010 | Pourmand et al. |
| 7,834,344 B2 | 11/2010 | Mascolo et al. |
| 7,851,045 B2 | 12/2010 | Gandon et al. |
| 7,886,601 B2 | 2/2011 | Merassi et al. |
| 7,901,629 B2 | 3/2011 | Calatzis et al. |
| 7,943,394 B2 | 5/2011 | Flandre et al. |
| 8,241,508 B2 | 8/2012 | D'Urso |
| 8,313,633 B2 | 11/2012 | Li et al. |
| 8,351,181 B1 | 1/2013 | Ahn |
| 8,591,816 B2 | 11/2013 | Calatzis et al. |
| 8,652,768 B1 | 2/2014 | Huber et al. |
| 8,753,893 B2 | 6/2014 | Liu et al. |
| 8,927,464 B2 | 1/2015 | Aizenberg et al. |
| 8,940,663 B2 | 1/2015 | Iqbal et al. |
| 9,070,733 B2 | 6/2015 | Rajagopal et al. |
| 9,108,880 B2 | 8/2015 | Jin et al. |
| 9,139,614 B2 | 9/2015 | Medintz |
| 9,306,164 B1 | 4/2016 | Chang et al. |
| 9,829,456 B1 | 11/2017 | Merriman et al. |
| 9,956,743 B2 | 5/2018 | Jin et al. |
| 10,036,064 B2 | 7/2018 | Merriman et al. |
| 10,125,420 B2 | 11/2018 | Jin et al. |
| 10,151,722 B2 | 12/2018 | Jin et al. |
| 10,508,296 B2 | 12/2019 | Merriman et al. |
| 10,526,696 B2 | 1/2020 | Jin et al. |
| 10,584,410 B2 | 3/2020 | Jin et al. |
| 10,597,767 B2 | 3/2020 | Merriman et al. |
| 10,712,334 B2 | 7/2020 | Choi et al. |
| 2002/0022223 A1 | 2/2002 | Connolly |
| 2002/0090649 A1 | 7/2002 | Chan et al. |
| 2002/0137083 A1 | 9/2002 | Kobori et al. |
| 2002/0138049 A1 | 9/2002 | Allen et al. |
| 2002/0142150 A1 | 10/2002 | Baumann et al. |
| 2002/0142477 A1 | 10/2002 | Lewis et al. |
| 2002/0172963 A1 | 11/2002 | Kelley et al. |
| 2002/0184939 A1 | 12/2002 | Yadav |
| 2003/0025133 A1 | 2/2003 | Brousseau |
| 2003/0040000 A1 | 2/2003 | Connolly et al. |
| 2003/0040173 A1 | 2/2003 | Fonash |
| 2003/0064390 A1 | 4/2003 | Schülein et al. |
| 2003/0087296 A1 | 5/2003 | Fujita et al. |
| 2003/0109031 A1 | 6/2003 | Chafin et al. |
| 2003/0141189 A1 * | 7/2003 | Lee ..................... C12Q 1/6869 204/600 |
| 2003/0141276 A1 | 7/2003 | Lee et al. |
| 2003/0186263 A1 | 10/2003 | Frey et al. |
| 2003/0224387 A1 | 12/2003 | Kunwar et al. |
| 2004/0014106 A1 | 1/2004 | Patno et al. |
| 2004/0023253 A1 | 2/2004 | Kunwar et al. |
| 2004/0038090 A1 | 2/2004 | Faris |
| 2004/0048241 A1 | 3/2004 | Freeman et al. |
| 2004/0063100 A1 | 4/2004 | Wang |
| 2004/0086929 A1 | 5/2004 | Weide et al. |
| 2004/0096866 A1 | 5/2004 | Hoffman et al. |
| 2004/0012161 A1 | 6/2004 | Chiu |
| 2004/0146863 A1 | 7/2004 | Pisharody et al. |
| 2004/0209355 A1 | 10/2004 | Edman et al. |
| 2004/0209435 A1 | 10/2004 | Patridge et al. |
| 2004/0229247 A1 | 11/2004 | DeBoer et al. |
| 2004/0235016 A1 | 11/2004 | Hamers |
| 2004/0248282 A1 | 12/2004 | Sobha |
| 2005/0029227 A1 | 2/2005 | Chapman |
| 2005/0067086 A1 | 3/2005 | Ito et al. |
| 2005/0074911 A1 | 4/2005 | Kornilovich et al. |
| 2005/0151541 A1 | 7/2005 | Brinz et al. |
| 2005/0156157 A1 | 7/2005 | Parsons et al. |
| 2005/0164371 A1 | 7/2005 | Arinaga |
| 2005/0172199 A1 | 8/2005 | Miller et al. |
| 2005/0181195 A1 | 8/2005 | Dubrow |
| 2005/0221473 A1 | 10/2005 | Dubin et al. |
| 2005/0227373 A1 | 10/2005 | Flandre et al. |
| 2005/0247573 A1 | 11/2005 | Nakamura et al. |
| 2005/0285275 A1 | 12/2005 | Son |
| 2005/0287548 A1 | 12/2005 | Bao et al. |
| 2005/0287589 A1 | 12/2005 | Connolly |
| 2006/0003482 A1 | 1/2006 | Chinthakindi et al. |
| 2006/0019273 A1 | 1/2006 | Connolly et al. |
| 2006/0024504 A1 | 2/2006 | Nelson et al. |
| 2006/0024508 A1 | 2/2006 | D'Urso et al. |
| 2006/0029808 A1 | 2/2006 | Zhai et al. |
| 2006/0051919 A1 | 3/2006 | Mascolo et al. |
| 2006/0051946 A1 | 3/2006 | Mascolo et al. |
| 2006/0105449 A1 | 5/2006 | Larmer et al. |
| 2006/0105467 A1 | 5/2006 | Niksa et al. |
| 2006/0128239 A1 | 5/2006 | Nun et al. |
| 2006/0147983 A1 | 7/2006 | O'uchi |
| 2006/0154489 A1 | 7/2006 | Tornow |

(56) References Cited

U.S. PATENT DOCUMENTS

| | | |
|---|---|---|
| 2006/0275853 A1 | 12/2006 | Matthew et al. |
| 2007/0026193 A1 | 2/2007 | Luzinov et al. |
| 2007/0048748 A1 | 3/2007 | Williams et al. |
| 2007/0140902 A1 | 6/2007 | Calatzis et al. |
| 2007/0148815 A1 | 6/2007 | Chao et al. |
| 2007/0186628 A1 | 8/2007 | Curry et al. |
| 2007/0184247 A1 | 9/2007 | Simpson et al. |
| 2007/0207487 A1 | 9/2007 | Emig et al. |
| 2007/0231542 A1 | 10/2007 | Deng |
| 2008/0012007 A1 | 1/2008 | Li et al. |
| 2008/0098815 A1 | 5/2008 | Merassi et al. |
| 2008/0149479 A1 | 6/2008 | Olofsson et al. |
| 2008/0199657 A1 | 8/2008 | Capron et al. |
| 2008/0199659 A1 | 8/2008 | Zhao |
| 2009/0011222 A1 | 1/2009 | Xiu et al. |
| 2009/0017571 A1 | 1/2009 | Nuckolls |
| 2009/0020428 A1 | 1/2009 | Levitan |
| 2009/0027036 A1 | 1/2009 | Nuckolls et al. |
| 2009/0062684 A1 | 3/2009 | Gregersen et al. |
| 2009/0152109 A1 | 6/2009 | Whitehead et al. |
| 2009/0162927 A1 | 6/2009 | Naaman et al. |
| 2009/0170716 A1 | 7/2009 | Su et al. |
| 2009/0178935 A1 | 7/2009 | Reymond et al. |
| 2009/0295372 A1 | 12/2009 | Krstic et al. |
| 2009/0297913 A1 | 12/2009 | Zhang et al. |
| 2009/0306578 A1 | 12/2009 | Sivan et al. |
| 2009/0324308 A1 | 12/2009 | Law et al. |
| 2010/0038342 A1 | 2/2010 | Lim et al. |
| 2010/0044212 A1 | 2/2010 | Kim et al. |
| 2010/0055397 A1 | 3/2010 | Kurihara et al. |
| 2010/0132771 A1 | 6/2010 | Lu |
| 2010/0142259 A1 | 6/2010 | Drndic et al. |
| 2010/0149530 A1 | 6/2010 | Tomaru |
| 2010/0167938 A1 | 7/2010 | Su et al. |
| 2010/0184062 A1 | 7/2010 | Steinmueller-Nethl et al. |
| 2010/0188109 A1 | 7/2010 | Edel et al. |
| 2010/0194409 A1 | 8/2010 | Gao et al. |
| 2010/0201381 A1 | 8/2010 | Iqbal et al. |
| 2010/0206367 A1 | 8/2010 | Jeong et al. |
| 2010/0227416 A1 | 9/2010 | Koh et al. |
| 2010/0280397 A1 | 11/2010 | Feldman et al. |
| 2010/0285275 A1 | 11/2010 | Baca et al. |
| 2010/0285601 A1 | 11/2010 | Kong et al. |
| 2010/0288543 A1 | 11/2010 | Hung et al. |
| 2010/0300899 A1 | 12/2010 | Levine et al. |
| 2011/0044857 A1* | 2/2011 | Lin .................. B82Y 15/00 422/69 |
| 2011/0056845 A1 | 3/2011 | Stellacci |
| 2011/0065588 A1 | 3/2011 | Su et al. |
| 2011/0076783 A1 | 3/2011 | Liu et al. |
| 2011/0091787 A1 | 4/2011 | McGrath et al. |
| 2011/0160077 A1 | 6/2011 | Chaisson et al. |
| 2011/0166034 A1 | 7/2011 | Kwong et al. |
| 2011/0217763 A1 | 9/2011 | Rasooly et al. |
| 2011/0227558 A1 | 9/2011 | Mannion et al. |
| 2011/0229667 A1 | 9/2011 | Jin et al. |
| 2011/0233075 A1 | 9/2011 | Soleymani et al. |
| 2011/0248315 A1 | 10/2011 | Nam et al. |
| 2011/0287956 A1 | 11/2011 | Iqbal et al. |
| 2011/0291673 A1 | 12/2011 | Shibata et al. |
| 2011/0311853 A1 | 12/2011 | Fratti |
| 2011/0312529 A1 | 12/2011 | He et al. |
| 2012/0060905 A1 | 3/2012 | Fogel et al. |
| 2012/0122715 A1 | 5/2012 | Gao et al. |
| 2012/0220046 A1 | 8/2012 | Chao |
| 2012/0258870 A1 | 10/2012 | Schwartz et al. |
| 2012/0286332 A1 | 11/2012 | Rothberg et al. |
| 2012/0309106 A1 | 12/2012 | Eichen et al. |
| 2013/0049158 A1 | 2/2013 | Hong et al. |
| 2013/0071289 A1 | 3/2013 | Knoll |
| 2013/0108956 A1 | 5/2013 | Lu et al. |
| 2013/0109577 A1 | 5/2013 | Korlach et al. |
| 2013/0162276 A1 | 6/2013 | Lee et al. |
| 2013/0183492 A1 | 7/2013 | Lee et al. |
| 2013/0214875 A1 | 8/2013 | Duncan et al. |
| 2013/0239349 A1 | 9/2013 | Knights et al. |
| 2013/0245416 A1 | 9/2013 | Yarmush et al. |
| 2013/0273340 A1 | 10/2013 | Neretina et al. |
| 2013/0281325 A1 | 10/2013 | Elibol et al. |
| 2013/0299945 A1* | 11/2013 | Stolovitzky .......... C12Q 1/6874 257/618 |
| 2013/0331299 A1 | 12/2013 | Reda et al. |
| 2014/0001055 A1 | 1/2014 | Elibol et al. |
| 2014/0011013 A1 | 1/2014 | Jin |
| 2014/0018262 A1 | 1/2014 | Reda et al. |
| 2014/0048776 A1 | 2/2014 | Huang et al. |
| 2014/0054788 A1 | 2/2014 | Majima et al. |
| 2014/0057283 A1 | 2/2014 | Wang et al. |
| 2014/0061049 A1 | 3/2014 | Lo et al. |
| 2014/0079592 A1 | 3/2014 | Chang et al. |
| 2014/0027775 A1 | 6/2014 | Quick et al. |
| 2014/0170567 A1 | 6/2014 | Sakamoto et al. |
| 2014/0174927 A1 | 6/2014 | Bashir et al. |
| 2014/0197459 A1 | 7/2014 | Kis et al. |
| 2014/0218637 A1 | 8/2014 | Gao et al. |
| 2014/0235493 A1 | 8/2014 | Zang et al. |
| 2014/0253827 A1 | 9/2014 | Gao et al. |
| 2014/0284667 A1 | 9/2014 | Basker et al. |
| 2014/0320849 A1 | 10/2014 | Chou et al. |
| 2014/0367749 A1 | 12/2014 | Bai et al. |
| 2014/0377900 A1 | 12/2014 | Yann et al. |
| 2015/0005188 A1 | 1/2015 | Levner et al. |
| 2015/0017655 A1 | 1/2015 | Huang et al. |
| 2015/0049332 A1 | 2/2015 | Sun et al. |
| 2015/0057182 A1 | 2/2015 | Merriman et al. |
| 2015/0065353 A1 | 3/2015 | Turner et al. |
| 2015/0068892 A1 | 3/2015 | Ueno et al. |
| 2015/0077183 A1 | 3/2015 | Ciubotaru |
| 2015/0148264 A1 | 5/2015 | Esfandyarpour et al. |
| 2015/0177150 A1 | 6/2015 | Rothberg et al. |
| 2015/0191709 A1 | 7/2015 | Heron et al. |
| 2015/0263203 A1 | 9/2015 | Lewis et al. |
| 2015/0293025 A1 | 10/2015 | Ninomiya et al. |
| 2015/0294875 A1 | 10/2015 | Khondaker et al. |
| 2015/0344945 A1 | 12/2015 | Mandell et al. |
| 2016/0017416 A1 | 1/2016 | Boyanov et al. |
| 2016/0045378 A1 | 2/2016 | Geloen |
| 2016/0155971 A1 | 6/2016 | Strachan et al. |
| 2016/0187282 A1 | 6/2016 | Gardner et al. |
| 2016/0265047 A1 | 9/2016 | van Rooyen et al. |
| 2016/0284811 A1 | 9/2016 | Yu et al. |
| 2016/0290957 A1 | 10/2016 | Ram |
| 2016/0319342 A1 | 11/2016 | Kawai et al. |
| 2016/0377564 A1 | 12/2016 | Carmignani et al. |
| 2017/0023512 A1 | 1/2017 | Cummins et al. |
| 2017/0037462 A1 | 2/2017 | Turner et al. |
| 2017/0038333 A1 | 2/2017 | Turner et al. |
| 2017/0043355 A1 | 2/2017 | Fischer |
| 2017/0044605 A1 | 2/2017 | Merriman |
| 2017/0131237 A1 | 5/2017 | Ikeda |
| 2017/0184542 A1 | 6/2017 | Chatelier et al. |
| 2017/0234825 A1 | 8/2017 | Elibol et al. |
| 2017/0240962 A1 | 8/2017 | Merriman |
| 2017/0288017 A1 | 10/2017 | Majima et al. |
| 2017/0332918 A1 | 11/2017 | Keane |
| 2018/0014786 A1 | 1/2018 | Keane |
| 2018/0031508 A1 | 2/2018 | Jin |
| 2018/0031509 A1 | 2/2018 | Jin |
| 2018/0045665 A1 | 2/2018 | Jin |
| 2018/0259474 A1 | 9/2018 | Jin |
| 2018/0297321 A1 | 10/2018 | Jin et al. |
| 2018/0305727 A1 | 10/2018 | Merriman |
| 2018/0340220 A1 | 11/2018 | Merriman |
| 2019/0004003 A1 | 1/2019 | Merriman |
| 2019/0033244 A1 | 1/2019 | Jin |
| 2019/0039065 A1 | 2/2019 | Choi |
| 2019/0041355 A1 | 2/2019 | Merriman |
| 2019/0041378 A1 | 2/2019 | Choi |
| 2019/0094175 A1 | 3/2019 | Merriman |
| 2019/0194801 A1 | 6/2019 | Jin et al. |
| 2019/0355442 A1 | 11/2019 | Merriman et al. |
| 2019/0376925 A1 | 12/2019 | Choi et al. |
| 2019/0383770 A1 | 12/2019 | Choi et al. |
| 2020/0157595 A1 | 5/2020 | Merriman et al. |

(56) References Cited

U.S. PATENT DOCUMENTS

| | | | |
|---|---|---|---|
| 2020/0217813 A1 | 7/2020 | Merriman et al. |
| 2020/0242482 A1 | 7/2020 | Merriman et al. |
| 2020/0277645 A1 | 9/2020 | Merriman et al. |
| 2020/0385850 A1 | 12/2020 | Merriman et al. |
| 2020/0385855 A1 | 12/2020 | Jin et al. |
| 2020/0393440 A1 | 12/2020 | Jin et al. |

FOREIGN PATENT DOCUMENTS

| | | |
|---|---|---|
| CN | 102706940 | 10/2012 |
| CN | 104685066 | 6/2015 |
| CN | 104703700 | 6/2015 |
| CN | 108027335 | 5/2018 |
| DE | 102012008375 | 10/2012 |
| DE | 102013012145 | 1/2015 |
| EP | 2053383 | 4/2009 |
| EP | 3403079 | 11/2018 |
| EP | 3408219 | 12/2018 |
| EP | 3408220 | 12/2018 |
| EP | 3414784 | 12/2018 |
| EP | 3420580 | 1/2019 |
| GB | 2485559 | 5/2012 |
| JP | H0233981 | 7/1990 |
| JP | 2008-258594 | 10/2008 |
| JP | 2018-522236 | 8/2018 |
| KR | 20070059880 | 6/2007 |
| KR | 20110104245 | 9/2011 |
| WO | 2001044501 | 6/2001 |
| WO | 2002049980 | 6/2002 |
| WO | 2002074985 | 9/2002 |
| WO | 2003042396 | 5/2003 |
| WO | 2004096986 | 11/2004 |
| WO | 2004099307 | 11/2004 |
| WO | 2005108612 | 11/2005 |
| WO | 2007054649 | 5/2007 |
| WO | 2007102960 | 9/2007 |
| WO | 2007126432 | 11/2007 |
| WO | 2007128965 | 11/2007 |
| WO | 2009003208 | 1/2009 |
| WO | 2009035647 | 3/2009 |
| WO | 2010022107 | 2/2010 |
| WO | 2012083249 | 6/2012 |
| WO | 2012087352 | 6/2012 |
| WO | 2012152056 | 11/2012 |
| WO | 2013096851 | 6/2013 |
| WO | 2014182630 | 7/2014 |
| WO | 2015167019 | 11/2015 |
| WO | 2015176990 | 11/2015 |
| WO | 2015188197 | 12/2015 |
| WO | 2016016635 | 2/2016 |
| WO | 2016100635 | 6/2016 |
| WO | 2016100637 | 6/2016 |
| WO | 2016196755 | 12/2016 |
| WO | 2016210386 | 12/2016 |
| WO | 2017027518 | 2/2017 |
| WO | 2017041056 | 3/2017 |
| WO | 2017042038 | 3/2017 |
| WO | 2017061129 | 4/2017 |
| WO | 2017123416 | 7/2017 |
| WO | 2017132567 | 8/2017 |
| WO | 2017132586 | 8/2017 |
| WO | 2017139493 | 8/2017 |
| WO | 2017147187 | 8/2017 |
| WO | 2017151680 | 9/2017 |
| WO | 2017184677 | 10/2017 |
| WO | 2018022799 | 2/2018 |
| WO | 2018026855 | 2/2018 |
| WO | 2018098286 | 5/2018 |
| WO | 2018132457 | 7/2018 |
| WO | 2018136148 | 7/2018 |
| WO | 2018200687 | 11/2018 |
| WO | 2018208505 | 11/2018 |
| WO | 2003091458 | 1/2019 |

OTHER PUBLICATIONS

USPTO; Requirement for Restriction dated Jan. 17, 2017 in U.S. Appl. No. 15/336,557.
USPTO; Advisory Action dated Mar. 14, 2017 in U.S. Appl. No. 15/050,270.
USPTO; Non-Final Office Action dated May 16, 2017 in U.S. Appl. No. 15/336,557.
USPTO; Final Office Action dated Dec. 30, 2016 in U.S. Appl. No. 15/050,270.
USPTO; Non-Final Office Action dated Sep. 29, 2017 in U.S. Appl. No. 15/050,270.
USPTO; Non-Final Office Action dated Oct. 19, 2016 in U.S. Appl. No. 15/220,307.
USPTO; Notice of Allowance dated Jul. 28, 2017 in U.S. Appl. No. 15/220,307.
USPTO; Requirement for Restriction dated Dec. 1, 2016 in U.S. Appl. No. 13/996,477.
USPTO; Non-Final Office Action dated May 5, 2017 in U.S. Appl. No. 13/996,477.
USPTO; Final Office Action dated Oct. 4, 2017 in U.S. Appl. No. 13/996,477.
USPTO; Notice of Allowance dated Jan. 3, 2018 in U.S. Appl. No. 13/996,477.
USPTO; Non-Final Office Action dated Feb. 9, 2018 in U.S. Appl. No. 15/728,400.
USPTO; Non-Final Office Action dated Feb. 23, 2018 in U.S. Appl. No. 15/728,412.
USPTO; Non-Final Office Action dated Feb. 23, 2018 in U.S. Appl. No. 15/796,080.
USPTO; Final Office Action dated Mar. 8, 2018 in U.S. Appl. No. 15/336,557.
USPTO; Notice of Allowance dated May 25, 2018 in U.S. Appl. No. 15/336,557.
USPTO; Final Office Action dated Jun. 13, 2018 in U.S. Appl. No. 15/728,412.
USPTO; Final Office Action dated Jun. 14, 2018 in U.S. Appl. No. 15/796,080.
USPTO; Final Office Action dated Jul. 10, 2018 in U.S. Appl. No. 15/050,270.
USPTO; Final Office Action dated Jul. 10, 2018 in U.S. Appl. No. 15/728,400.
USPTO; Advisory Action dated Sep. 4, 2018 in U.S. Appl. No. 15/796,080.
USPTO; Non-Final Office Action dated Sep. 4, 2018 in U.S. Appl. No. 15/979,135.
USPTO; Notice of Allowance dated Sep. 12, 2018 in U.S. Appl. No. 15/728,412.
USPTO; Advisory Action dated Sep. 26, 2018 in U.S. Appl. No. 15/050,270.
USPTO; Non-Final Office Action dated Sep. 28, 2018 in U.S. Appl. No. 12/667,583.
USPTO; Notice of Allowance dated Oct. 11, 2018 in U.S. Appl. No. 15/796/080.
USPTO; Advisory Action dated Oct. 12, 2018 in U.S. Appl. No. 15/728,400.
USPTO; Requirement for Restriction dated Oct. 15, 2018 in U.S. Appl. No. 16/015,028.
USPTO; Advisory Action dated Nov. 14, 2018 in U.S. Appl. No. 15/728,400.
USPTO; Non-Final Office Action dated Nov. 30, 2018 in U.S. Appl. No. 15/979,135.
USPTO; Notice of Allowance dated Dec. 6, 2018 in U.S. Appl. No. 15/728,400.
USPTO; Requirement for Restriction dated Dec. 17, 2018 in U.S. Appl. No. 16/015,049.
USPTO; Non-Final Office Action dated Dec. 26, 2018 in U.S. Appl. No. 16/015,028.
USPTO; Non-Final Office Action dated Feb. 1, 2019 in U.S. Appl. No. 16/152,190.
USPTO; Final Office Action dated Feb. 19, 2019 in U.S. Appl. No. 12/667,583.

(56) References Cited

OTHER PUBLICATIONS

USPTO; Non-Final Office Action dated Feb. 26, 2019 in U.S. Appl. No. 15/050,270.
USPTO; Final Office Action dated Mar. 1, 2019 in U.S. Appl. No. 15/979,135.
USPTO; Non-Final Office Action dated Mar. 6, 2019 in U.S. Appl. No. 16/015,049.
USPTO; Non-Final Office Action dated Mar. 7, 2019 in U.S. Appl. No. 15/944,356.
USPTO; Final Office Action dated Apr. 15, 2019 in U.S. Appl. No. 16/015,028.
USPTO; Advisory Action dated May 22, 2019 in U.S. Appl. No. 15/979,135.
USPTO; Restriction Requirement dated May 29, 2019 in U.S. Appl. No. 16/250,929.
USPTO; Notice of Allowance dated May 30, 2019, in U.S. Appl. No. 16/152,190.
USPTO; Final Office Action dated Jun. 19, 2019 in U.S. Appl. No. 16/015,049.
USPTO; Non-Final Office Action dated Jun. 25, 2019 in U.S. Appl. No. 15/979,135.
USPTO; Final Office Action dated Jul. 10, 2019 in U.S. Appl. No. 15/050,270.
USPTO; Non-Final Office Action dated Jul. 30, 2019 in the U.S. Appl. No. 16/015,028.
USPTO; Non-Final Office Action dated Aug. 22, 2019 in the U.S. Appl. No. 16/011,065.
USPTO; Restriction Requirement dated Sep. 19, 2019 in U.S. Appl. No. 16/073,706.
USPTO; Non-Final Office Action dated Aug. 19, 2019 in U.S. Appl. No. 12/667,583.
USPTO; Notice of Allowance dated Oct. 23, 2019 in U.S. Appl. No. 16/250,929.
USPTO; Non-Final Office Action dated Oct. 24, 2019 in U.S. Appl. No. 16/073,706.
USPTO; Notice of Allowance dated Nov. 8, 2019 in U.S. Appl. No. 16/015,028.
USPTO; Non-Final Office Action dated Nov. 5, 2019 in U.S. Appl. No. 16/015,049.
USPTO; Notice of Allowance dated Dec. 11, 2019 in U.S. Appl. No. 15/979,135.
USPTO; Notice of Allowance dated Jan. 6, 2020 in U.S. Appl. No. 15/050,270.
USPTO; Non-Final Office Action dated Jan. 10, 2020 in U.S. Appl. No. 16/076,673.
USPTO; Final Office Action dated Mar. 6, 2020 in U.S. Appl. No. 16/011,065.
USPTO; Notice of Allowance dated Feb. 20, 2020 in U.S. Appl. No. 16/015,049.
USPTO; Non-Final Office Action dated Apr. 13, 2020 in U.S. Appl. No. 16/070,133.
USPTO; Restriction Requirement dated Apr. 8, 2020 in U.S. Appl. No. 16/479,257.
USPTO; Notice of Allowance dated May 11, 2020 in U.S. Appl. No. 16/073,706.
USPTO; Notice of Allowance dated Jun. 1, 2020 in U.S. Appl. No. 16/076,673.
USPTO; Non-Final Office Action dated Jun. 2, 2020 in U.S. Appl. No. 16/684,338.
USPTO; Non-Final Office Action dated Jun. 15, 2020 in U.S. Appl. No. 16/878,484.
USPTO; Non-Final Office Action dated Jun. 30, 2020 in U.S. Appl. No. 16/479,257.
USPTO; Non-Final Office Action dated Jun. 30, 2020 in U.S. Appl. No. 16/477,106.
PCT; International Search Report and Written Opinion dated Nov. 29, 2012 in Application No. PCT/US2011/001995.
PCT; International Search Report and Written Opinion dated Jan. 27, 2017 in Application No. PCT/US2017/015465.
PCT; International Search Report and Written Opinion dated Jan. 27, 2017 in Application No. PCT/US2017/015437.
PCT; International Search Report and Written Opinion dated Jul. 26, 2017 in Application No. PCT/US2017/017231.
PCT; International Search Report and Written Opinion dated May 25, 2017 in Application No. PCT/US2017/018950.
PCT; International Search Report and Written Opinion dated Sep. 27, 2016 in Application No. PCT/US2016/039446.
PCT; International Search Report and Written Opinion dated Nov. 22, 2017 in Application No. PCT/US2017/044023.
PCT; International Search Report and Written Opinion dated Dec. 26, 2017 in Application No. PCT/US2017/044965.
PCT; International Search Report and Written Opinion dated Mar. 7, 2018 in Application No. PCT/US2017/063105.
PCT; International Search Report and Written Opinion dated Mar. 12, 2018 in Application No. PCT/US2017/063025.
PCT; International Search Report and Written Opinion dated Apr. 13, 2018 in Application No. PCT/US2018/013140.
PCT; International Search Report and Written Opinion dated Jul. 20, 2018 in Application No. PCT/US2018/029382.
PCT; International Search Report and Written Opinion dated Jul. 20, 2018 in Application No. PCT/US2018/029393.
PCT; International Search Report and Written Opinion received Nov. 9, 2018 in Application No. PCT/US2018/048873.
PCT; International Search Report and Written Opinion dated Apr. 8, 2010 in Application No. PCT/US2009/054235.
PCT; International Search Report and Written Opinion dated Jan. 18, 2019 in Application No. PCT/US2018/055264.
PCT; International Search Report and Written Opinion dated Apr. 18, 2017 in Application No. PCT/US2016/068922.
EP; European Search Report dated Jan. 30, 2019 in Application No. EP16815467.2.
CN; Notice of the First Office Action dated Sep. 2, 2019 in Chinese Application No. 201680049272.8.
EP; European Search Report dated Aug. 2, 2019 in Application No. EP16885434.7.
EP; European Search Report dated Aug. 2, 2019 in Application No. EP17745026.9.
CN; Notice of the First Office Action dated Sep. 30, 2019 in Chinese Application No. 201780020478.2.
EP; European Search Report dated Oct. 24, 2019 in Application No. 17757146.
PCT; International Preliminary Report on Patentability dated Oct. 29, 2019 in Application No. PCT/US2018/029382.
EP; European Search Report dated Jan. 29, 2020 in Application No. 17745013.7.
EP; European Search Report dated Jan. 29, 2020 in Application No. 17750776.1.
EP; European Search Report dated Feb. 7, 2020 in Application No. 17837566.3.
EP; European Search Report dated Mar. 6, 2020 in Application No. 17835231.6.
EP; European Search Report dated Jun. 18, 2020 in Application No. 16815467.2.
CN; Office Action dated Jun. 5, 2020 in Chinese Patent Application No. 2017800204782.
EP; European Search Report dated Jun. 26, 2020 in Application No. 17874229.2.
Ahn et al., "Electrical Immunosensor Based on a Submicron-Gap Interdigitated Electrode and Gold Enhancement," Biosensors and Bioelectronics, vol. 26, pp. 4690-4696, (2011).
Alayo et al., "Gold Interdigitated Nanoelectrodes as a Sensitive Analytical Tool for Selective Detection of Electroactive Species via Redox Cycling," Microchim Acta, vol. 183, pp. 1633-1639, (2016).
Antibody Structure Downloaded from https://absoluteantibody.com/antibody-resources/antibody-overview/antibody-structure/ (Mar. 1, 2019).
Bai et al., "Review: Gas Sensors Based on Conducting Polymers," Sensors, vol. 7, pp. 267-307, (2007).
Bailey et al., "DNA-Encoded Antibody Libraries: A Unified Platform for Multiplexed Cell Sorting and Detection of Genes and Proteins," Journal of American Chemical Society, vol. 129, pp. 1959-1967, (2007).

(56) References Cited

OTHER PUBLICATIONS

Bechelany et al. "Synthesis Mechanisms of Organized Nanoparticles: Influence of Annealing Temperature and Atmosphere," Crystal Growth and Design, vol. 10, pp. 587-596 (Oct. 21, 2010).
Berdat et al., "Label-Free Detection of DNA with Interdigitated Micro-Electrodes in a Fluidic Cell," Lab on a Chip, vol. 8, pp. 302-308, (2008).
Bhura, "3D Interdigitated Electrode Array (IDEA) Biosensor for Detection of Serum Biomarker," Master Thesis, Portland State University, 68 Pages, (2011).
Blossey, R., "Self-Cleaning Surfaces-Virtual Realities," Nature Materials, vol. 2(5), pp. 301-306, (May 2006).
Bonilla et al., "Electrical Readout of Protein Microarrays on Regular Glass Slides," Analytical Chemistry, vol. 83, pp. 1726-1731, (2011).
Botsialas et al., "A Miniaturized Chemocapacitor System for the Detection of Volatile Organic Compounds," Sensors and Actuators B, Chemical, vol. 177, pp. 776-784, (2013).
Branagan et al., "Enhanced Mass Transport of Electroactive Species to Annular Nanoband Electrodes Embedded in Nanocapillary Array Membranes," Journal of the American Chemical Society, vol. 134, pp. 8617-8624, (2012).
Braun et al., "DNA-Templated Assembly and Electrode Attachment of a Conducting Silver Wire," Letters to Nature, vol. 391(6669), pp. 775-778, (Feb. 1998).
Briglin et al., "Exploitation of Spatiotemporal Information and Geometric Optimization of Signal/Noise Performance Using Arrays of Carbon Black-Polymer Composite Vapor Detectors," Sensors and Actuators B, vol. 82, pp. 54-74, (2002).
Cassie, A.B.D. et al., "Wettability of Porous Surfaces," Transitions of the Faraday Society, vol. 40, pp. 546-551, (Jan. 1944) (Abstract Only).
Cerofolini et al., "A Hybrid Approach to Nanoelectronics: A Hybrid Approach to Nanoelectrics," Nanotechnology, Institute of Physics Publishing, GB, vol. 16, No. 8, pp. 1040-1047 (2005).
Chen et al., "Electrochemical Approach for Fabricating Nanogap Electrodes with Well Controllable Separation," Applied Physics Letters, vol. 86, pp. 123105.1-123105.3, (2005).
Chen, X. et al., "Electrical Nanogap Devices for Biosensing," Materials Today, vol. 13, pp. 28-41, (Nov. 2010).
Chen et al., "Fabrication of Submicron-Gap Electrodes by Silicon Volume Expansion for DNA-Detection," Sensors and Actuators A, vol. 175, pp. 73-77, (2012).
Choi Y.S. et al., "Hybridization by an Electroatomical Genome on Detection on Using an Indicator-Free DNA on a Microelectrode-Array DNA Chip," Bulletin of the Korean Chemistry Society, vol. 26, pp. 379-383, (2005).
Choi, J. E. et al., "Fabrication of Microchannel with 60 Electrodes and Resistance Measurement," Flow Measurement and Instrumentation, vol. 21, pp. 178-183, (Sep. 2010) (Abstract Only).
Choi, C. et al., "Strongly Superhydrophobic Silicon Nanowires by Supercritical CO2 Drying," Electronic Materials Letters, vol. 6 (2), pp. 59-64, (Jun. 2010).
Church et al., "Next-Generation Digital Information Storage in DNA," Science, vol. 337(6102), p. 6102, (Sep. 28, 2012).
Cosofret et al., "Microfabricated Sensor Arrays Sensitive to pH and K+ for Ionic Distribution Measurements in the Beating Heart," Analytical Chemistry, vol. 67, pp. 1647-1653, (1995).
Coulson S.R. et al., "Super-Repellent Composite Fluoropolymer Surfaces," The Journal of Physical Chemistry B., vol. 104(37), pp. 8836-8840, (Aug. 2000).
Dickey et al., "Electrically Addressable Parallel Nanowires with 30 NM Spacing from Micromolding and Nanoskiving," Nano Letters, vol. 8(12), pp. 4568-4573, (2008).
Fan et al., "Detection of MicroRNAs Using Target-Guided Formation of Conducting Polymer Nanowires in Nanogaps," Journal of the American Chemical Society, vol. 129, pp. 5437-5443, (2007).
Fink et al. "Electrical Conduction Through DNA Molecules," Nature, vol. 398, pp. 407-410 (Jan. 20, 1999).

Fuller et al., "Real-Time Single-Molecule Electronic DNA Sequencing by Synthesis Using Polymer-Tagged Nucleotides on a Nanopore Array," Proceedings of the National Academy of Sciences, vol. 113(19), pp. 5233-5523, (May 10, 2016).
Gapin, A.I. et al., "CoPt Patterned Media in Anodized Aluminum Oxide Templates," Journal of Applied Physics, vol. 99(8), pp. 08G902 (1-3), (Apr. 2006).
Ghindilis, A. et al., "Real Time Biosensor Platforms Fully Integrated Device for Impedimetric Assays," ECS Transactions, vol. 33, pp. 59-68, (2010).
Guo et al., "Conductivity of a single DNA duplex bridging a carbon nanotube gap," Nat. Nanotechnol., vol. 3, No. 3, pp. 1-12 (2008).
Han, "Energy Band Gap Engineering of Graphene Nanoribbons," Physical Review Letters, vol. 98, pp. 1-7, (May 16, 2007).
Han et al., "Redox Cycling in Nanopore-Confined Recessed Dual-Ring Electrode Arrays," Journal of Physical Chemistry C, vol. 120, pp. 20634-20641, (2016).
Hanief, Topic, Pineda-Vargas, "Solid State Dewetting of Continuous Thin Platinum Coatings," Nuclear Instruments and Methods in Physics Research, vol. 363, pp. 173-176, (2015).
Hashioka et al., "Deoxyribonucleic Acid Sensing Device with 40-NM-Gap-Electrodes Fabricated by Low-Cost Conventional Techniques," Applied Physics Letters, vol. 85(4), p. 687-688, (Jul. 2004).
He et al., "Electromechanical Fabrication of Atomically Thin Metallic Wires and Electrodes Separated with Molecular-Scale Gaps," Journal of Electroanalytical Chemistry, vol. 522, pp. 167-172, (Jan. 2002).
Heerema et al., "Graphene Nanodevices for DNA Sequencing," Nature Nanotechnology, vol. 11, pp. 127-136, (Feb. 3, 2016).
Henry et al., "Microcavities Containing Individually Addressable Recessed Microdisk and Tubular Nanoband Electrodes," Journal of the Electrochemical Society, vol. 146(9), pp. 3367-3373, (1999).
Hwang et al., "Electrical Transport Through 60 Base Pairs of Poly (dG)-Poly (dC) DNA Molecules," Applied Physics Letters, vol. 81(6), p. 1134-1136, (Aug. 2002).
Ino et al., "Addressable Electrode Array Device with IDA Electrodes for High-Throughput Detection," Lab on a Chip, vol. 11, p. 385-388, (2011).
Ino et al., "Local Redox-Cycling-Based Electrochemical Chip Device with Seep Microwells for Evaluation of Embryoid Bodies," Angewandte Chemie International Edition, vol. 51, pp. 6648-6652, (2012).
Iqbal et al., "Direct Current Electrical Characterization of ds-DNA in Nanogap Junctions," Applied Physics Letter, vol. 86, p. 153901-1-153901-3, (Apr. 2005).
Javey et al., "Layer-By-Layer Assembly of Nanowires for Three-Dimensional, Multifunctional Electronics," Nano Letters, vol. 7, pp. 773-777, (2007).
Khawli et al., "Charge Variants in IgG1-Isolation, Characterization, In Vitro Binding Properties and Pharmacokinetics in Rats," Landes Bioscience, vol. 2(6), pp. 613-623, (2010).
Kim et al., "Rapid Fabrication of Uniformly Sized Nanopores and Nanopore Arrays for Parallel DNA Analysis," Advances Materials, vol. 18, pp. 3149-3153, (Dec. 4, 2006).
Kim, J. Y. et al., "Optically Transparent Glass with Vertically Aligned Surface AI203 Nanowires Having Superhydrophobic Characteristics," NANO: Brief Reports and Reviews, vol. 5(2), pp. 89-95, (Apr. 2010) (Abstract Only).
Kitsara et al., "Single Chip Interdigitated Electrode Capacitive Chemical Sensor Arrays," Sensors and Actuators B, vol. 127, pp. 186-192, (2007).
Kitsara et al., "Small-Volume Multiparametric Electrochemical Detection at Low Cost Polymeric Devices Featuring Nanoelectrodes," SPIE, vol. 9518, 9 Pages, (2015).
Kraft, "Doped Diamond: A Compact Review on a New, Versatile Electrode Material," International Journal of Electrochemistry, vol. 2, pp. 355-385, (May 2007).
Kumar et al., "Terminal Phosphate Labeled Nucleotides: Synthesis, Applications and Linker Effect on Incorporation by DNA Polymerases," Nucleosides, Nucleotides and Nucleic Acids, Taylor and Francis, vol. 24, No. 5-7, pp. 401-408 (2005).

(56) References Cited

OTHER PUBLICATIONS

Lee, K. H. et al., "One-Chip Electronic Detection of DNA Hybridization using Precision Impedance-Based CMOS Array Sensor," Biosensors and Bioelectronics, vol. 26, pp. 1373-1379, (Dec. 15, 2010).
Li et al., "Graphene Channel Liquid Container Field Effect Transistor as pH Sensor," Hindawi Publishing Corp., Journal of Nanomaterials 2014.
Lin et al., "An Addressable Microelectrode Array for Electrichemical Detection," Analytical Chemistry, vol. 80, pp. 6830-6833, (2008).
Liu et al., "Controllable Nanogap Fabrication on Microchip by Chronopotentiometry," Electrochimica Acta, vol. 50, pp. 3041-3047, (2005).
Liu et al., "Atomically Thin Molybdenum Disulfide Nanopores with High Sensitivity for DNA Translocation," ACS Nano, vol. 8, pp. 2504-2511, (Feb. 18, 2014).
Liu et al., "An Enzyme-Based E-DNA Sensor for Sequence-Specific Detection of Femtomolar DNA Targets," J. Am. Chem. Soc., vol. 130(21), pp. 6820-6825, (2008).
MacNaughton et al., "High-Throughput Heterogeneous Integration of Diverse Nanomaterials on a Single Chip for Sensing Applications," PLOS One, vol. 9(10), e111377, 7 Pages, (2014).
Mastrototaro et al., "Thin-Film Flexible Multielectrode Arrays for Voltage Measurements in the Heart," IEEE Engineering in Medicine & Biology Society 11th Annual International Conference, 1 Page, (1989).
Mastrototaro et al., "Rigid and Flexible Thin-Film Multielectrode Arrays for Transmural Cardiac Recording," IEEE Transactions on Biomedical Engineering, vol. 39, pp. 217-279, (1992).
Mirando-Castro et al., "Hairpin-DNA Probe for Enzyme-Amplified Electrochemical Detection of Legionella pnuemophila," Anal. Chem., vol. 79, pp. 4050-4055, (Jun. 1, 2007).
Nishida, A. et al. "Self-Oriented Immobilization of DNA Polymerase Tagged by Titanium-Binding Peptide Motif," Langmuir, vol. 31, pp. 732-740 (Dec. 17, 2014).
Niwa, O. et al., "Fabrication and Characteristics of Vertically Separated Interdigitated Array Electrodes," Journal of Electroanalytical Chemistry and Interfacial Electrochemistry, vol. 267 pp. 291-297, (Aug. 10, 1989) (Abstract Only).
Okinaka et al., ""Polymer" Inclusions in Cobalt-Hardened Electroplated Gold," Journal the of Electrochemical Society, vol. 125, p. 1745, (1978). (Abstract Only).
Park, S.J. et al., "Array-Based Electrical Detection of DNA with Nanoparticle Probes," Science, vol. 295, pp. 1503-1506, (Feb. 22, 2002).
Park, C.W. et al., "Fabrication of Poly-Si/ AU Nano-Gaps Using Atomic-Layer-Deposited $Al_2O_3$ as a Sacrificial Layer," Nanotechnology, vol. 16, pp. 361-364, (Feb. 1, 2005)(Abstract Only).
Parkin, I. P. et al., "Self-Cleaning Coatings," Journal of Materials Chemistry, vol. 15(17), pp. 1689-1695, (Dec. 2004).
Prins et al., "Room-Temperature Gating of Molecular Junctions Using Few-Layer Graphene Nanogap Electrodes," Nano Letters, vol. 11, pp. 4607-4611, (Oct. 21, 2011).
Pugliese et al., "Processive Inforporation of Deoxynucleoside Triphosphate Analogs by Single-Molecule DNA Polymerase I (Klenow Fragment) Nanocircuits," Journal of the American Chemical Society, vol. 137, No. 30, pp. 9587-9594 (2015).
Qing et al., "Finely Tuning Metallic Nanogap Size with Electrodeposition by Utilizing High-Frequency Impedance in Feedback," Angewandte Chemie Int ed, vol. 44, pp. 7771-7775, (2005).
Reed et al., "Conductance of a Molecular Junction Reports," Science, vol. 278, pp. 252-254, (Oct. 1997).
Roy, S. et al., "Mass-Produced Nanogap Sensor Arrays for Ultra-Sensitive Detection of DNA," Journal of the American Chemical Society, vol. 131, pp. 12211-12217, (Aug. 5, 2009) (Abstract Only).
Reichert et al., "Driving Current Through Single Organic Molecules," Physical Review Letters, vol. 88(17), pp. 176804-1-176804-4, (Apr. 2002).
Roppert et al., "A New Approach for an Interdigitated Electrodes DNA-Sensor," XVIIIth International Symposium on Bioelectrochemistry and Bioenergetics, Bioelectrochemistry, p. 143, (2005).
Ruttkowski, E. et al., "CMOS based Arrays of Nanogaps Devices for Molecular Devices," Proceedings of 2005 5th IEEE Conference on Nanotechnology, vol. 1, pp. 438-441, (Jul. 2005) (Abstract Only).
Sanguino et al., "Interdigitated Capacitive Immunosensors with PVDF Immobilization Layers," IEEE Sensors Journal, vol. 14(4), pp. 1260-1265, (Apr. 2014).
Santschi et al., "Interdigitated 50nm Ti Electrode Arrays Fabricated using $XeF_2$ Enhanced Focused Ion Beam Etching," Nanotechnology, vol. 17, pp. 2722-2729, (2006).
Schaefer et al., "Stability and Dewetting Kinetics of Thin Gold Films on Ti, TiOx, and ZnO Adhesion Layers," Acta Materialia, vol. 61, pp. 7841-7848, (2013).
Schrott, W. et al., "Metal Electrodes in Plastic Microfluidic Systems," Microelectronic Engineering, vol. 86, pp. 1340-1342, (Jun. 2009).
Shimanovsky et al., "Hiding Data in DNA," International Workshop on Information Hiding, Lecture Notes in Computer Science, pp. 373-386, (Dec. 18, 2012).
Shimoda, T. et al., "Solution-Processed Silicon Films and Transistors," Nature, vol. 440(7085), pp. 783-786, (Apr. 2006).
Sholders et al., "Distinct Conformations of a Putative Translocation Element in Poliovirus Polymerase," Journal of Molecular Biology, vol. 426(7), pp. 1407-1419, (Apr. 3, 2014).
Singh et al., "3D Nanogap Interdigitated Electrode Array Biosensors," Analytical and Bioanalytical Chemistry, vol. 397, pp. 1493-1502, (2010).
Singh et al., "Evaluation of Nanomaterials-Biomolecule Hybrids for Signals Enhancement of Impedimetric Biosensors," 11th IEEE International Conference on Nanotechnology, pp. 707-710, (2011).
Singh et al., "Nanoparticle-Enhanced Sensitivity of a Nanogap-Interdigitated Electrode Array Impedimetric Biosensor," Langmuir, vol. 27, pp. 13931-13939, (2011).
Stagni, C. et al., "CMOS DNA Sensor Array with Integrated A/D Conversation Based on Label-Free Capacitance Measurement," IEEE Journal of Solid-State Circuits, vol. 41, pp. 2956-2964, (Nov. 20, 2006).
Stenning, "The Investigation of Grain Boundary Development and Crystal Synthesis of Thin Gold Films on Silicon Wafers," http://www.ucl.ac.uk/~ucapikr/projects, (Mar. 31, 2009).
Su, Y., "Modeling and Characteristic Study of Thin Film Based Biosensor Based on COMSOL," Mathematical Problems in Engineering, Article 581063 (6 Pages), (Apr. 7, 2014).
Thompson, "Solid-State Dewetting of ThinFilms," Department of Materials Science and Engineering, vol. 42, pp. 399-434, (2012).
Urban, M. et al., "A Paralleled Readout System for an Electrical DNA-Hybridization Assay Based on a Microstructured Electrode Array," Review of Scientific Instruments, vol. 74, pp. 1077-1081, (Jan. 2003) (Abstract Only).
Van Gerwin et al., "Nanoscaled Interdigitated Electrode Arrays for Biochemical Sensors," Sensors and Actuators B, vol. 49, pp. 73-80, (1998).
Van Megan et al., "Submicron Electrode Gaps Fabricated by Gold Electrodeposition at Interdigitated Electrodes," Key Engineering Materials, vol. 605, pp. 107-110, (2014).
Wang et al., "Electronics and Optoelectronics of Two-Dimensional Transition Metal Dichalcogenides," Nature Nanotechnology, vol. 7, pp. 699-712, (Nov. 6, 2012).
Xu et al., "Fabrication of Complex Metallic Nanostructures by Nanoskiving," American Chemical Society Nano, vol. 1(3), pp. 215-227, (2007).
Zafarani et al., "Electrochemical Redox Cycling in a New Nanogap Sensor: Design and Simulation," Journal of Electroanalytical Chemistry, vol. 760, pp. 42-47, (2015).
USPTO; Non-Final Office Action dated Sep. 22, 2020 in U.S. Appl. No. 16/639,716.
USPTO; Non-Final Office Action dated Oct. 2, 2020 in U.S. Appl. No. 16/073,693.

(56) References Cited

OTHER PUBLICATIONS

USPTO; Non-Final Office Action dated Nov. 9, 2020 in U.S. Appl. No. 16/731,749.
PCT; International Search Report and Written Opinion dated Jun. 9, 2020 in Application No. PCT/US2020/13218.
PCT; International Search Report and Written Opinion dated Aug. 6, 2020 in Application No. PCT/US2020/25068.
PCT; International Search Report and Written Opinion dated Sep. 4, 2020 in Application No. PCT/US2020/28004.
EP; European Search Report dated Sep. 30, 2020 in Application No. 17893481.6.
JP; Office Action dated Aug. 13, 2020 in Japanese Application No. 2017-566864.
CN; Office Action dated Aug. 14, 2020 in Chinese Patent Application No. 201680083636.4.
Yang et al., "Two-Dimensional Graphene Nanoribbons," J. Am. Chem. Soc. vol. 130, Issue 13 (2008).
USPTO; Notice of Allowance dated Nov. 24, 2020 in U.S. Appl. No. 16/477,106.
USPTO; Notice of Allowance dated Dec. 7, 2020 in U.S. Appl. No. 16/878,484.
USPTO; Final Office Action dated Dec. 14, 2020 in U.S. Appl. No. 16/684,338.
USPTO; Final Office Action dated Jan. 6, 2021 in U.S. Appl. No. 16/070,133.
USPTO; Final Office Action dated Jan. 11, 2021 in U.S. Appl. No. 16/479,257.
USPTO; Non-Final Office Action dated Dec. 15, 2020 in U.S. Appl. No. 16/831,722.
USPTO; Non-Final Office Action dated Dec. 30, 2020 in U.S. Appl. No. 16/652,672.
EP; European Search Report dated Nov. 19, 2020 in Application No. 18739158.6.
JP; Office Action dated Dec. 2, 2020 in Japanese Patent Application No. 2018-536737.
EP; European Search Report dated Dec. 23, 2020 in Application No. 18790713.4.
EP; European Search Report dated Dec. 14, 2020 in Application No. 18799263.1.
Ali et al., "DNA hybridization detection using less than 10-nm gap silicon nanogap structure," Sensors and Actuators A. vol. 199, pp. 304-309 (2013).
Bornholt et al., "A DNA-Based Archival Storage System", Architectural Support For Programming Languages and Operating Systems, pp. 637-649 (2016).
Chen et al., "Silicon nanowire field-effect transistor-based biosensors for biomedical diagnosis and cellular recording investigation", Nano Today, Elsevier, Amsterdam, NL, vol. 6, No. 2, pp. 131-154 (2011).
Grass et al., "Robust Chemical Preservation of Digital Information on DNA in Silica with Error-Correcting Codes", Angewandte Chemie International Edition, vol. 54, No. 8, pp. 2552-2555 (2015).
Hatcher et al., "PNA versus DNA: Effects of Structural Fluctuations on Electronic Structure and Hole-Transport Mechanisms," J. Amer. Chem. Soc., 130, pp. 11752-11761 (2008).
Korlach et al., "Real-time DNA sequencing from single polymerase molecules," 11, Methods in Enzymology, Academy Press, vol. 472, pp. 431-455 (2010).
Paul et al., "Charge transfer through Single-Stranded Peptide Nucleic Acid Composed of Thymine Nucleotides," J. Phy. Chem. C 2008, 112, pp. 7233-7240 (2008).
Shin et al., "Distance Dependence of Electron Transfer Across Peptides with Different Secondary Structures: The Role of Peptide Energetics and Electronic Coupling," J. Amer. Chem. Soc. 2003, 125, pp. 3722-3732 (2003).
Venkatramani et al., "Nucleic Acid Charge Transfer: Black, White and Gray," Coard Chem Rev., 255(7-8): pp. 635-648 (2011).

\* cited by examiner

MASSIVELY PARALLEL DNA SEQUENCING APPARATUS

CROSS-REFERENCE TO RELATED APPLICATIONS

This application is a continuation of U.S. application Ser. No. 16/073,706, filed on Jul. 27, 2018 and entitled MASSIVELY PARALLEL DNA SEQUENCING APPARATUS," (now U.S. Pat. No. 10,712,334), which is a U.S. national phase filing under 35 U.S.C. § 371 of PCT/US2017/015437 filed on Jan. 27, 2017 and entitled "MASSIVELY PARALLEL DNA SEQUENCING APPARATUS", which claims priority to U.S. Provisional Application No. 62/288,364, filed on Jan. 28, 2016 and entitled "MASSIVELY PARALLEL DNA SEQUENCING APPARATUS COMPRISING STRONGLY ADHERED CONDUCTOR NANOTIPS AND NANOPILLARS, METHOD OF FABRICATION, AND APPLICATIONS THEREOF," the disclosures of which are incorporated herein by reference.

FIELD

This disclosure relates generally to nanotechnology, nanofabrication and nanoelectronics, and more particularly to systems, devices, and processes for electronic sensing and analyzing of individual biomolecules, including DNA and proteins.

BACKGROUND

Since the discovery of DNA, there has been a concerted effort to develop means to actually experimentally measure the sequences of the constitutive chemical bases. The first method for systematically sequencing DNA was introduced by Sanger in 1978.

This basic method was automated in a commercial instrument platform in the late 1980's, enabling the sequencing of the first human genome. The success of this effort motivated the development of a number of "massively parallel" sequencing platforms, with the goal of dramatically reducing the cost and time required to sequence a human genome. They generally rely on processing millions to billions of sequencing reactions at the same time, in highly miniaturized microfluidic formats.

This has been followed by a variety of other related techniques and commercial platforms. As it stands, further improvements in quality and accuracy of sequencing, as well as reductions in cost and time are still highly desirable. This is especially true to make genome sequencing practical for widespread use in precision medicine, where it is desirable to sequence the genomes of millions of individuals with a clinical grade of quality.

While many DNA sequencing techniques utilize optical means with fluorescence reporters, such methods can be cumbersome, slow in detection speed, and difficult to mass produce and reduce costs. Label-free DNA or genome sequencing approaches have advantages of not having to use fluorescent type labeling processes and associated optical systems, especially when combined with electronic signal detection that can be achieved rapidly and in an inexpensive way.

SUMMARY

Aspects of the present disclosure provide compositions and means of manufacture for nano-electrode systems, which are usable in electronic DNA sequencing systems. Such nano-electrode systems may also be used in analyzing other types of biomolecules, such as proteins, depending on how the nano-electrodes are functionalized to interact with biomolecule sensing targets. In general, the nano-electrode systems disclosed herein may be part of a system for such biomolecule analysis, wherein the nano-electrode system is coupled to biomolecules to constitute a molecular electronics sensor having specific application to sensing and characterizing a biomolecule target, in particular applications to sequencing of a DNA molecule, or a collection of such molecules constituting an entire genome.

In various embodiments of the present disclosure, a sequencing structure, such as usable for DNA or genome sequencing, includes: (a) an electrode pair, each electrode having a tip-shaped end, with the electrodes separated by a nanogap defined by the tip-shaped ends facing one another; (b) at least one conductive island deposited at or near each tip-shaped end of each electrode; and (c) a biomolecule having two ends, each end attached to the at least one conductive island on each electrode such that one biomolecule bridges the nanogap, wherein nucleotide interactions with the biomolecule provides for electronic monitoring of DNA or genome sequencing without the use of a fluorescing element. In various aspects, the electrode pair may be platinum (Pt), palladium (Pd), rhodium (Rh), gold (Au) or titanium (Ti), and the at least one conductive island may be gold (Au). In various examples, each end of a biomolecule is attached to at least one conductive island through antibody-antigen coupling or streptavidin-biotin coupling. In other examples, a biomolecule is attached to at least one conductive island through thiol-gold (Au) binding or gold binding proteins.

In various embodiments, the at least one conductive island may comprise gold (Au) based nano-tips obtained by electrodeposition of gold (Au) at or near each tip-shaped end of each electrode, optionally followed by post-deposition annealing. The at least one conductive island may be in the shape of a pillar grown on each electrode through an electrodeposition process, and each of these pillars may measure less than 20 nm in diameter and less than 25 nm in height, or in other embodiments, less than 7 nm in diameter and less than 10 nm in height. In other embodiments, the at least one conductive island may comprise electrodeposited or electroless deposited metal, such as Au, to form a nano-tip shaped or nano-pillar shaped conductive island having an exposed dimension, such as for biomolecule binding, measuring less than 20 nm.

In various embodiments of the present disclosure, conductive islands, such as electrodeposited or electroless deposited Au nano-tips or nano-pillars, may be modified so as to increase the surface area of the tip or pillar. For example, a nano-tip or nano-pillar may be modified to comprise a branched or porous surface, having a porosity of at least 30% so as to increase the surface area of an exposed surface of the nano-tip or nano-pillar by at least by 10% as compared to the nano-tip or nano-pillar structure after electrodeposition or electroless deposition.

In various embodiments of the present disclosure, a plurality of layers of electrode pairs may be arranged into three-dimensional arrays. Further, electrode pairs may be connected to one another such that one electrode from each pair are ganged together by a common lead wire and each of the other electrodes in each pair are left unconnected to one another, enabling independent and sequential interrogation of each electrode pair.

In various embodiments of the present disclosure, a genome or DNA sequencing system is disclosed. The system includes a DNA or genome sequencing structure such as set forth herein; and a chamber encasing the structure and defining a microfluidic subsystem usable to supply biomolecules, nucleotides, PBS, or water solutions to the electrode pair.

In various embodiments of the present disclosure, a method of making a genome or DNA sequencing device is disclosed. The method includes (a) disposing an array of electrode pairs on a substrate, each electrode within a given pair of electrodes having a tip-shaped end, with the electrodes in each pair separated by a nanogap defined by tip-shaped ends facing one another; (b) electrodepositing gold (Au) at each tip-shaped end by applying a voltage to the electrode pair whereby high current density in the region of each tip-shaped end of each electrode directs preferential electrodeposition of gold (Au) to each tip-shaped end to form a gold (Au) nano-tip on each electrode; and (c) attaching each end of a biomolecule having two ends to the gold (Au) nano-tips such that one biomolecule bridges over each nanogap in each electrode pair. The electrode pairs may comprise platinum (Pt), palladium (Pd) or rhodium (Rh), and the substrate may comprise silicon (Si) with a $SiO_2$ insulator surface. The method may further involve heat treating the array of electrode pairs after step (b) at from about 200 to about 800° C. to induce additional diffusional bonding of gold (Au) to the metal electrodes. In other examples, the method may further include patterning a passivation layer over the array of electrode pairs, prior to step (c), in order to cover undesired Au deposits present in locations other than at or near the tip-shaped ends of the electrodes.

In various aspects of the present disclosure, a method of making a genome or DNA sequencing device is disclosed. The method includes (a) disposing an array of electrode pairs on a substrate, each electrode within a given pair of electrodes having an end, with the electrodes in each pair separated by a nanogap defined by the ends of the electrodes facing one another; (b) disposing a mask resist layer over the electrodes; (c) nano-patterning the mask resist layer to form openings, one opening per electrode, wherein each opening is at or near each nanogap; (d) electrodepositing gold (Au) on each electrode through each opening to form gold (Au) nano-pillars; and (e) attaching each end of a biomolecule having two ends to the gold (Au) nano-pillars such that one biomolecule bridges over each nanogap in each electrode pair. The electrode pairs may comprise platinum (Pt), palladium (Pd) or rhodium (Rh), and the substrate may comprise silicon (Si) with a $SiO_2$ insulator surface. A resist layer used in this method may be PMMA or hydrogen silsesquioxane (HSQ). In this way, the gold (Au) nano-pillars grow within each opening as each opening is filled by the electrodeposition of gold (Au).

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the drawing figures.

Figure 1:
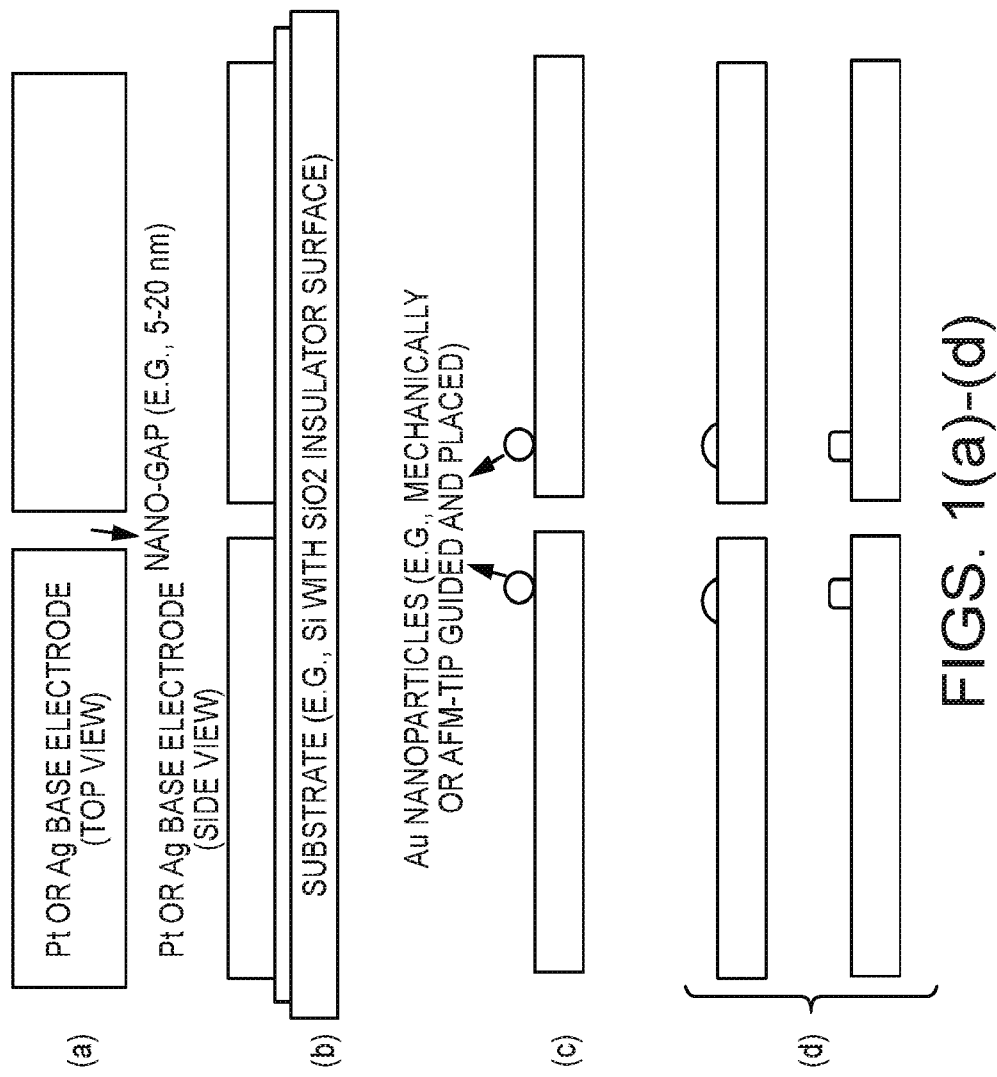
FIGS. 1(a)-(d) illustrate genome sequencing compatible electrodes having a structure comprising a 5-20 nm nanogap, with a pair of Au islands for attaching or immobilizing biomolecules thereon such as proteins or fragmented DNA for the purpose of fluorescence-free (i.e., label-free) detection of nucleotide attachments via electrical measurements.

It is to be understood that the drawings are for purposes of illustrating the concepts of the invention and are not to scale.

DETAILED DESCRIPTION

The detailed description of exemplary embodiments herein makes reference to the accompanying drawings, which show exemplary embodiments by way of illustration and their best mode. While these exemplary embodiments are described in sufficient detail to enable those skilled in the art to practice the invention, it should be understood that other embodiments may be realized and that logical, chemical, and mechanical changes may be made without departing from the spirit and scope of the inventions. Thus, the detailed description herein is presented for purposes of illustration only and not of limitation. For example, unless otherwise noted, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

The present disclosure generally describes a DNA or genome sequencing device, methods of making such devices, and methods of use. In various aspects of the present disclosure, a DNA or genome sequencing device has a structure comprising: (a) an electrode pair, wherein each electrode in the pair is fashioned with a tip-shaped end, and the electrodes in the pair are separated by a nanogap defined by the tip-shaped end of each electrode facing one another; (b) at least one conductive island deposited at or near each tip-shaped end of each electrode; and (c) a biomolecule, such a double stranded DNA molecule, having two ends, with each end attached to the conductive island on each electrode such that one biomolecule bridges the nanogap. Thus, each device comprises one pair of electrodes and one bridging biomolecule, and the biomolecule is bound at each of its ends to the conductive island portion of each electrode. In various aspects, such a device may be used in DNA or genome sequencing by electronically monitoring nucleotide interactions with the biomolecule. The biomolecule may further comprise a probe molecule linked to the biomolecule wherein the probe molecule, such as a polymerase enzyme, binds nucleotides to create electronic events that are sensed. In this way, DNA or genome sequencing is carried out without the use of a fluorescing element.

In various embodiments, each electrode is comprised of a conducting metal such as, for example, platinum (Pt), palladium (Pd), rhodium (Rh), gold (Au) or titanium (Ti). Also, the electrode pairs are disposed on a substrate, such as silicon (Si). The substrate may further comprise an insulating layer, such as silicon dioxide ($SiO_2$). A gate electrode (i.e. a third electrode), may be disposed under or adjacent to each nanogap, wherein each device comprises a three electrode structure, and the three electrodes comprise a circuit used for electronic monitoring of molecular binding and interactions involving the bridge biomolecule. A plurality of devices may be disposed in an array comprising many devices (e.g., hundreds up to hundreds of millions). In various aspects, arrays of devices may be two-dimensional or three-dimensional, in the latter case comprising a plurality of layers forming an array architecture.

In arrays of devices, electrode pairs may be connected to one another such that one electrode from each pair are electrically connected together ("ganged together") by a common lead wire and each of the other electrodes from each pair are left unconnected to one another, enabling independent and sequential interrogation of each electrode pair.

In various aspects of the disclosure, the conductive islands deposited on each of the electrodes of a device may comprise gold (Au). As discussed herein, gold (Au) is amenable to electrodeposition and "electroless" deposition processes, and is useful in bonding organic molecules, such as through strong gold (Au)-sulfur (S) bonds. The sulfur substituent for binding to a Au island may be part of a thiol (—SH) substituent present at or near each end of a biomolecule, or a disulfide linkage in a biomolecule that is reduced to two —SH groups for binding. In various aspects, one Au island is deposited per electrode. In other aspects, at least one Au island is deposited per electrode.

In various embodiments, each end of a biomolecule may be attached to the at least one conductive island through antibody-antigen coupling, streptavidin-biotin coupling, thiol-Au binding, or by gold binding proteins.

In various embodiments, at least one conductive island may comprise Au based nano-tips obtained by electrodeposition of gold (Au) at or near each tip-shaped end of each electrode. Further, at least one conductive island may comprise Au based nano-tips obtained by electrodeposition of gold (Au) at or near each tip-shaped end of each electrode, followed by post-electrodeposition annealing. Also, Au islands may be electroless deposited, and the resulting islands may be post-electroless deposition annealed. As discussed here, annealing can increase the contact area of an island such as Au on an electrode, and can increase the bonding strength between Au island and electrode.

In various examples, at least one conductive island may be in the shape of a pillar, wherein the pillar is grown on each electrode through an electrodeposition process. Such pillars may measure: less than 20 nm in diameter and less than 25 nm in height each; less than 15 nm in diameter and less than 20 nm in height each; less than 10 nm in diameter and less than 15 nm in height each; or less than 7 nm in diameter and less than 10 nm in height each; or less than.

For any shape conductive island herein, a contact area between the conductive island and the electrode surface may be at least about 50%, and preferable up to 100% of the island diameter (or the island cross-sectional dimension). Thus, a pillar shaped conductive island of cylindrical shape, (i.e. having a round cross sectional area) may be in contact with the electrode at the entire bottom of the pillar, that is, across the entire cross sectional area. For a dot or spherical shaped conductive island, the contact area may be up to and including 100% of the diameter of the sphere, meaning the conductive island may comprise a hemispherical shape. In some instances, annealing may form what appears to be an Au metallized tip on the end of a tip-shaped electrode, such as the end of a pointed electrode.

In various embodiments of the present disclosure, the surface area of a conductive island can be increased, either by damaging the surface, removing portions of the surface, or otherwise making the surface more porous. In certain instances, a nano-tip or nano-pillar may comprise a branched or porous surface, having a porosity of at least 30% so as to increase the surface area of an exposed surface of the nano-tip or nano-pillar by at least by 10% as compared to the nano-tip or nano-pillar structure after electrodeposition or electroless deposition on each electrode. Gold islands may be modified to increase surface area such as by preparing a nanocomposite consisting of Au and included metallic nanoparticles such as Co, Ni, Fe, Cu, Zn, Al, Si, Mo, V, or ceramic nanoparticles such as CoO or $Co_2O_3$, NiO, $Fe_2O_3$ or $Fe_3O_4$, CuO, ZnO, $Al_2O_3$, $MoO_2$, $V_2O_5$, $SiO_2$ and preferentially etching away these metallic or ceramic or polymer nanoparticles or nano fibers, so as to produce a porosity of at least 30% preferably at least 50% so as to increase the surface area of gold element top surface by at least by 10%, preferably by at least 20%, even more preferably by at least 60% as compared with the straightforward Au nano-pillar structure. In other examples, a nanocomposite may comprise a mixture of Au and at least one of carbon nanotubes, graphene nano-flakes, polymer nanoparticles and nanofibers. Any of these non-Au materials may be subsequently burned away so as to produce a porosity in the Au of at least 10%, at least 20%, at least 30%, at least 40%, or preferably at least 50%, so as to increase the surface area of the top surface of the gold island by at least by 3%, at least 5%, at least 10%, at least 20%, at least 30%, at least 40%, at least 50%, or least 60%, over the porosity of a Au nano-pillar comprising only unmodified Au as obtained from Au electrodeposition.

In various embodiments, a DNA or genome sequencing system may comprise at least one of the devices as described herein (such as an array of devices) and a chamber encasing the device(s), such as to provide a microfluidic subsystem into which solutions can be administered to supply biomolecules, nucleotides, PBS, or water solutions to the one or more devices. Such systems allow convenient and controlled exposure of the electrode pairs to various solutions of molecules.

In various embodiments of the present disclosure, a method of making a genome or DNA sequencing device is disclosed. The method includes the steps of: disposing an array of electrode pairs on a substrate, each electrode within a given pair of electrodes having a tip-shaped end, with the electrodes in each pair separated by a nanogap defined by tip-shaped ends facing one another; electrodepositing gold (Au) at each tip-shaped end by applying a voltage to the electrode pair whereby high current density in the region of each tip-shaped end of each electrode directs preferential electrodeposition of gold (Au) to each tip-shaped end to form a gold (Au) nano-tip on each electrode; and attaching each end of a biomolecule having two ends to the gold (Au) nano-tips such that one biomolecule bridges over each nanogap in each electrode pair. The electrodes within each pair may comprise platinum (Pt), palladium (Pd) or rhodium (Rh), and the substrate may comprise silicon (Si) with a $SiO_2$ insulator surface. These methods may further involve heat treating the array of electrode pairs after depositing the gold at from about 200 to about 800° C. to induce additional diffusional bonding of the Au to the metal electrodes. Further, the methods may involve patterning a passivation layer over the array of electrode pairs prior to attaching a biomolecule to each pair in order to cover up undesired Au deposits that appeared in locations other than on or near the tip-shaped ends of the electrodes.

In other embodiments of the present disclosure, a method of making a genome or DNA sequencing device is disclosed. The method involves the steps of: disposing an array of electrode pairs on a substrate, each electrode within a given pair of electrodes having an end, with the electrodes in each pair separated by a nanogap defined by the ends of the electrodes facing one another; disposing a mask resist layer over the electrodes; nano-patterning the mask resist layer to form openings, one opening per electrode, wherein each opening is at or near each nanogap; electrodepositing gold (Au) on each electrode through each opening to form gold (Au) nano-pillars; and attaching each end of a biomolecule having two ends to the gold (Au) nano-pillars such that one biomolecule bridges over each nanogap in each electrode pair. Each electrode may comprise platinum (Pt), palladium (Pd) or gold (Au), and the substrate may comprise silicon (Si) with a $SiO_2$ insulator surface. In these methods, the resist layer may comprise PMMA or hydrogen silsesquioxane (HSQ). The gold (Au) nano-pillars grow within each opening with each opening filled layer by layer within each confined space by electrodeposition.

The drawing figures and various imaging show fabrication of the nano-sensor concepts disclosed herein, as well as embodiments of using such types of nano-electrodes in DNA sequence analysis. The figures and images supporting this disclosure include, but are not limited to: Molecular sensor for DNA sequence analysis; Test measurement set-up for nano-electrode molecular sensors; Nano-electrodes with gold contact islands used in molecular sensor work; Electrical monitoring of self-assembly on nano-electrodes; DNA sequencing signals from molecular electronic nano-electrode sensor; Fabricated gold island nano-electrodes; Fabricated gold-electroplated nano-electrodes; Passivation of fabricated nano-electrodes; and Fabricated multi-gold-bead linear ball-up array electrodes.

Referring now to the drawings, FIGS. 1(a)-(d) schematically illustrate sequencing genome compatible electrodes with a 5-20 nm nano-gap there between, each pair of gapped electrodes having a pair of Au islands, which are for attaching or immobilizing biomolecules, such as proteins or fragmented DNA, as bridges across the electrode pairs. Such a biomolecular bridged electrode structure is usable in fluorescence-free (i.e., label-free) detection of nucleotide attachments or other molecular interactions via electrical measurements. In more detail, FIG. 1(a) illustrates the top view of an embodiment of a single pair of electrodes separated by a nano-gap of from about 5 to about 20 nm. FIG. 1(b) illustrates a side view of an exemplary pair of electrodes on a substrate with an insulator surface. In this example, the substrate is Si and the insulator layer is $SiO_2$. Such electrode pairs are disclosed herein as usable within a device for genome/DNA sequencing through electronic conductance measurements. Each pair of electrodes is desirably made of high conductivity metal having stable and inert characteristics. Gold (Au), for example, is most widely used as an electrode material. However, within the scope of the present invention, alternative metals, such Pt, Pd, or Rh, are utilized so as to prevent non-specific random attachment of biomolecules (e.g., proteins or DNAs) on the electrode surface. By using a Pt base electrode, biomolecules are much less prone to attach directly on the Pt surface. Thus, with the addition of a pair of Au islands of several nanometer regime size, the attachment site of biomolecules, especially just a single biomolecule per one electrode, can be confined to the Au island rather than to areas of the electrode surface absent Au.

Unfortunately, small nanoparticles, such as ~5 nm diameter regime gold nanoparticles, are difficult to position and place on an electrode surface. Atomic Force Microscopy (AFM) may be used to pick-up and move an individual Au nanoparticle to the electrode surface, and deposit it thereon, whereby van der Walls forces keep the nanoparticle at its intended location, (see, for example, Huang, et al., U.S. Pat. App. Ser. No. 2014/0048776, published Feb. 20, 2014). However, such delicate movement and placement of nanoparticles, resulting for example in the structure illustrated in FIG. 1(c), can result in Au nanoparticles that are not particularly well adhered onto the electrode surface.

These structures wherein the nanoparticles are not strongly adhered to the electrode surfaces, (FIG. 1(c)), will exhibit high contact resistance and reduced electrical conductivity. Furthermore, such poorly attached Au nanoparticles can be easily moved laterally to a different location or detached permanently during washing, microfluidic processing of biomolecules, or other handling. Such AFM guided placement of a nanoparticle, one by one, is laborious, time consuming and not amenable to low-cost manufacturing. Therefore, according to the present invention, the Au nanoparticle is not just physically deposited on an electrode surface as is the case in the prior art (FIG. 1(c)), but rather is more strongly bonded onto the electrode surface such that the contact area of the Au particle used in the bonding with the electrode surface comprises at least 20%, at least 30%, at least 40%, at least 50%, at least 60%, at least 70%, preferably at least 80%, and even more preferably up to 100% of the Au particle diameter. Diagrammatically, this strong bonding between Au particles and electrode surface is illustrated in the two examples of FIG. 1(d).

For molecular electronics devices, including those usable for protein analysis or DNA/genome sequencing, parallel electronic sensing using an array comprising a plurality of electrode pair devices is highly desirable. In order to package more electrical measurement devices and circuits within a given space, the electrode dimensions must be reduced to micro- or nano-scale. For example, an array of nano-electrode geometry comprising electrode pairs in parallel arrangement can be utilized. Such an array can be made by using convenient and scalable processing methods such as nano-imprint lithography. Alternative methods such as e-beam lithography, self-assembly and other means may also be utilized.

Figure 2:
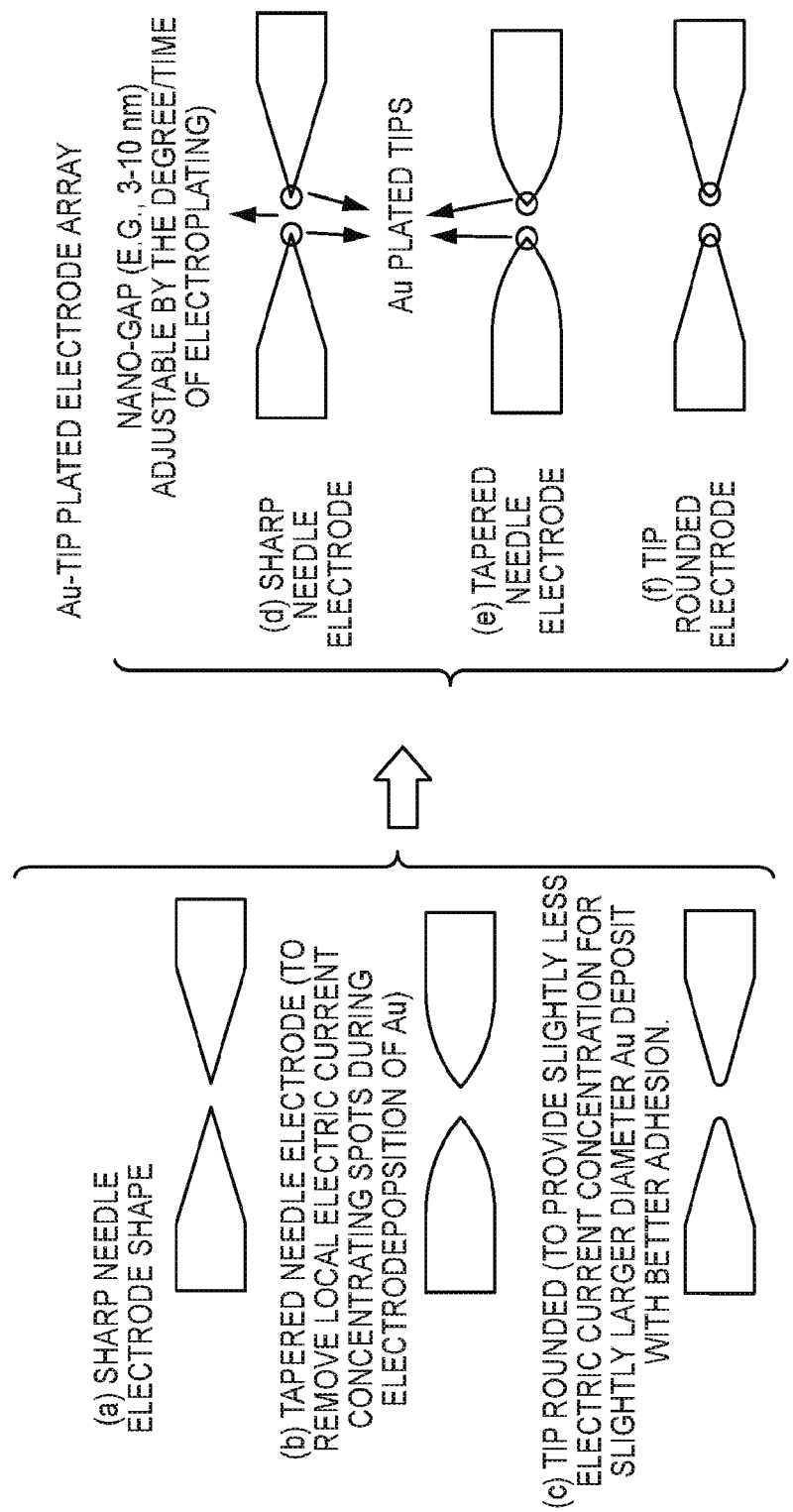
FIGS. 2(a)-(c) illustrate a top view of nano-electrode geometries having different shapes, such as produced by nano-imprint lithography, e-beam lithography, or other methods. Underlying substrate material, such as Si with Sift surface insulator, is not shown.
FIGS. 2(d)-(f) illustrate massively parallel, electrodeposited Au islands or other conductive islands by utilizing the sharp point with higher current density for preferential deposition at the tip location.

Referring again to the drawings, FIG. 2 describes one of the embodiments to create reliable Au islands on electrodes in an inexpensive, massively parallel way, by employing electrodeposition while the electrode array is electrically connected to a cathode and anode. As electrodeposition occurs on one electrode but not the other, the left side Pt (or Pd or Rh) electrode tip is electrodeposited with Au first, and then the right side tip is plated as cathode vs anode role during electrodeposition is reversed. Sharp edges, corners, tips or protruding portions of a conductive object, such as the Pt electrode tips in FIGS. 2(a)-(c), tend to have highly concentrated electrical current during electrodeposition. Hence, the electrode tips are plated with Au preferentially rather than other parts of the Pt electrodes which are not sharpened, tipped, or protruding. For electrodeposition on shaped electrodes, an exemplary electroplating solution includes, but is not limited to, potassium gold cyanide $(KAu(CN)_2)$ based solution. An example bath composition comprises 12-15 g/liter $KAu(CN)_2$, 90-115 g/liter citric acid, 0.07-0.1 g/liter cobalt (added as acetate or sulfate), with pH adjusted to 3.6-4.7 (e.g., with KOH), and bath temperature of 40-65° C., (see for example, Y. Okinaka, F. B. Koch, C. Wolowodiuk, and D. R. Blessington, *J. Electrochem. Soc.*, 125, 1745 (1978)). Non-cyanide electroplating baths are also usable herein, (see for example, *Modern Electroplating*, 5th Ed, edited by Mordechay Schlesinger and Milan Paunovic, Chapter 4, "Electrodeposition of Gold" by Paul A. Kohl, ISBN: 978-0-47046778-6 Dec. 2014, John Wiley & Sons, Inc.). Direct current (DC) electrodeposition or pulse deposition may be used, with the latter more convenient in accurately controlling the size of the electrodeposited gold.

In accordance with the present disclosure, the deposited Au region at the electrode tip is not a nanoparticle but is instead an integral part of the electrode structure, strongly adhered to the electrode by electrodeposition. Examples of electrode geometries suitable for electrodeposition of Au are set forth in FIGS. 2(a)-(c). FIGS. 2(a)-(c) illustrate top views of nano-electrode pair geometry with different shapes. These shapes are made by, for example, nano-imprint lithography for scaled-up manufacturing, e-beam lithography, or other known methods. Substrate material, such as Si with a $SiO_2$ surface insulator, residing under each electrode pair, is not shown for clarity. FIGS. 2(d)-(f) illustrate the variously shaped electrode tips electrodeposited with Au or other metal as conductive islands, by utilizing the sharp point, tip, or other protrusion of the electrode wherein the higher current density at those locations direct preferential deposition. For better results, any undesired sharp edges or irregularities on the base electrode are preferably removed to avoid inadvertent electrodeposition of Au at these irregularities in addition to the desired locations. Tapered and smoother side geometry of the electrode pair of FIG. 2(e) is one design to minimize undesirable Au deposition at locations other than at the electrode tips. In FIG. 2(f), slightly rounded tip design is disclosed, which is also useful when a slightly larger size Au tip deposition is desired.

Electrodeposition of Au or other conductive tips, particularly when electrode pairs are reacted in massively parallel fashion, is convenient and very practical compared to the prior art methods such as movement and placement of individual Au nanoparticles by an atomic force microscope (AFM) tip. Many devices (e.g., 1,000 to 10 million genome sequencing electrode devices) can be processed simultaneously. Post-anneal of the electrode deposition to enhance Au adhesion is an optional process. Heat treating of the entire electrode device array can be accomplished at temperatures of about 200 to about 800° C. in air, for about 10 mins to 12 hrs in vacuum or in an inert atmosphere, which induces additional diffusional bonding of Au to the substrate metal electrode. The Au tip processed by electrodeposition in accordance to the present invention is strongly adhered to the base electrode metal, wherein the contact area of the Au bonded to the electrode surface comprises at least 20%, at least 30%, at least 40%, at least 50%, at least 60%, at least 70%, preferably at least 80%, and even more preferably up to 100% of the Au particle diameter.

Although the sharp tip region of a pointed electrode is preferentially coated with Au during electrodeposition, and hence deposition of Au at other locations on the electrode is correspondingly rare, in some instances there can be deposition of Au at undesired locations. In case there is some inadvertent deposition of Au in any shape on other parts of the electrode surface other than the desired tip location (e.g. as illustrated in FIGS. 2(d)-(f)), an additional step of patterned coating of the electrodes at regions except the tip region may be performed, as illustrated in FIGS. 3(a) and 3(b).

FIG. 3(a) diagrammatically illustrates an Au tipped electrode array wherein inadvertent Au islands were electrodeposited in various undesired locations on the electrode surfaces. As mentioned, a patterned coating may be disposed on the electrodes thereafter to cover these undesired islands. FIG. 3(b) illustrates an exemplary patterned coating that masks the inadvertent Au island depositions to eliminate unwanted biomolecule attachments onto the electrode surface at these errant locations when the electrodes are exposed to biomolecules.

In various embodiments of the present invention, nano-sized gold can be electrodeposited in other configurations, such as protruding Au nano-pillars on Au electrodes, using masked electrodeposition on individual locations selected on the electrodes. In this process, the Au nano-pillars are grown at selected un-masked locations. The first step of the process is disposing a mask layer such as for example, PMMA or hydrogen silsesquioxane (HSQ) on the Au electrode surfaces and then nano-patterning the mask resist layer to form exposed openings or "holes." In the next step, massively parallel electrodeposition of Au in the form of protruding pillars can be grown by position-selected electrodeposition aided by the masked pattern. The holes patterned in the mask resist are typically 4-20 nm and preferably 6-10 nm in diameter and it is through each of these patterned holes where the gold is electrodeposited, as shown by the stepwise process of FIGS. 4(a)-(e).

Figure 4:
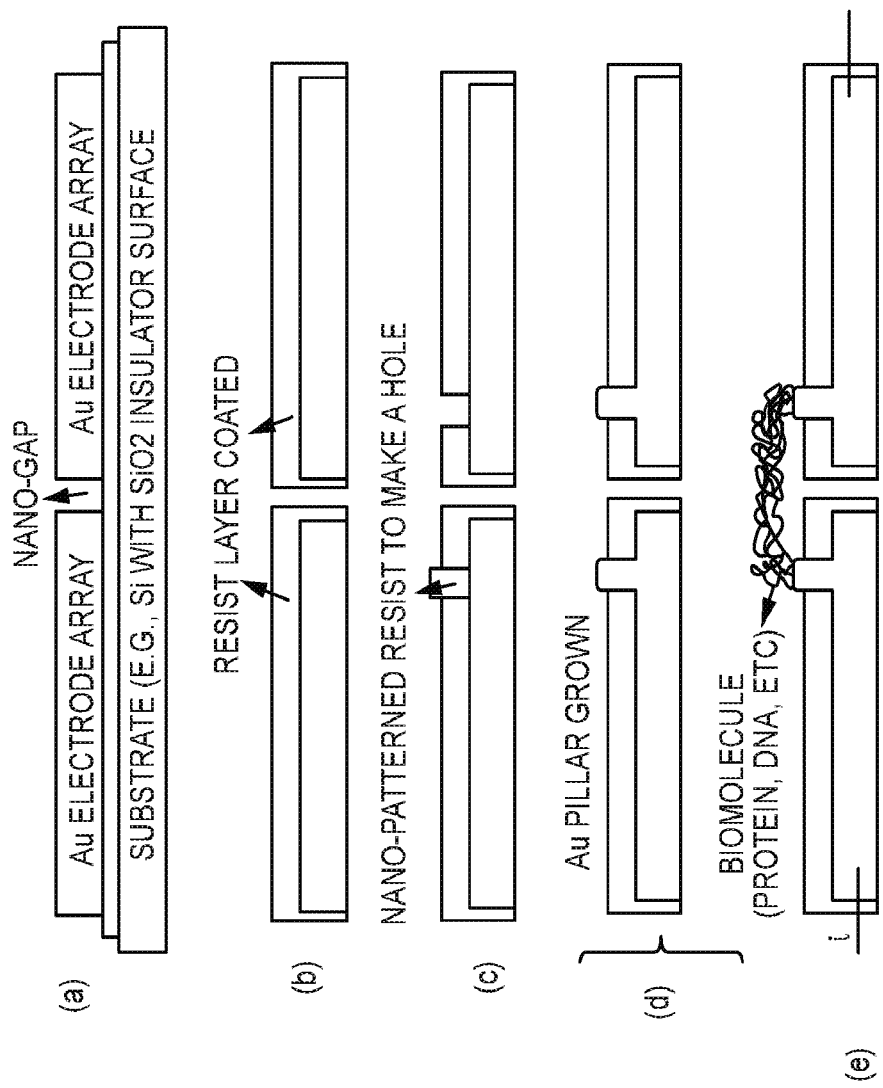
FIG. 4(a) illustrates a cross-sectional view of an exemplary Au electrode array.
FIGS. 4(b)-(c) illustrate the formation of nano-pillars using masked electrodeposition.
FIG. 4(d) illustrates a protruding Au pillar with good contact area.
FIG. 4(e) illustrates an exemplary use of Au pillar structure for molecular electronics devices.

As illustrated in the cross-sectional view of the exemplary Au electrode array in FIG. 4(a), large-areas of Au electrodes will not reliably serve as portions of a device to attract a single biomolecule, DNA fragment, or nucleotide for electrical interrogation because random, undesirable pluralities of biomolecules are likely to be attached on to each electrode due to the large exposed Au surfaces. Therefore, it is essential to have only a single nano-defined pillar on each electrode. The term "pillar" is used broadly herein to refer to three-dimensional structures with round, square, rectangular or any other cross-sectional shape. Such pillars are formed in the holes with the surrounding areas all masked, as illustrated in the steps of FIGS. 4(b) and 4(c). Positive resist (e.g., PMMA) or negative resist (e.g., HSQ, SU-8) coated by e-beam or nano-imprint lithography may be utilized for the nano-patterning to create a hole array. Nano-imprinting facilitates simultaneous fabrication of a large number of devices, for example, more than 10,000 devices.

For efficient and simultaneous creation of huge numbers of Au nano-pillars on Au or other conducting electrodes, electrical terminals for all the lead wires on the left electrodes, and all the lead wires on the right side of the device array with repeated electrode pattern device like the one illustrated in FIG. 4(c), are temporarily electrically connected, respectively to two separate common electrical paths, so that electrodeposition can be performed on all the electrodes simultaneously. This allows massively parallel electrodeposition of Au pillars for an easier, low-cost, mass manufacturing process. The number of Au pillars (which equal twice the number of electrode pair devices) that can be simultaneously created, according to the process thus described, is at least 100 devices, preferably at least 10,000 devices, and more preferably at least one million devices.

As the protruding gold pillar of FIG. 4(d) has a good contact area, comparable to the pillar diameter (or other cross-sectional width if not cylindrical), the electrical contact resistance is desirably very small. This is unlike the high contact resistance situation of prior-art nanoparticle attachments (e.g., Au nano-particles moved and deposited by an AFM probe tip). Also, the Au pillar thus grown is now a part of Au electrode base with gold on gold contacts, so very strong adhesion is ensured since there is only a single metal. These desirable characteristics of Au nano-pillar structure described herein are advantageous in minimizing noise in the electrical signal, e.g., during genome sequencing. The Au nano-pillar cross-sectional dimension (e.g. diameter) prepared by the method illustrated in FIGS. 4(a)-(d) is less than 20 nm, less than 15 nm, less 10 nm, or less than 7 nm. The height of the Au pillar is less than 25 nm, less than 20 nm, less than 15 nm, or less than 10 nm.

FIG. 4(e) illustrates an exemplary use of the Au pillar structure for molecular electronics devices, in accordance to a further aspect of the invention. Such Au pillar structure is useful for DNA and genome sequencing as well as protein analysis. FIG. 4(e) shows a single biomolecule (e.g., a protein, a DNA segment, etc.) attached onto the Au pillar surface for electrical interrogation during a molecular interaction, e.g., for example, nucleotide attachment to the biomolecule. The biomolecule attachment to the surface of the Au pillar is enabled by various functionalization and targeting attachments. These include, but are not limited to, antibody-antigen attraction or biotin-streptavidin conjugation, thiol-Au bonding, Au-binding peptides, or the like.

Figure 5:
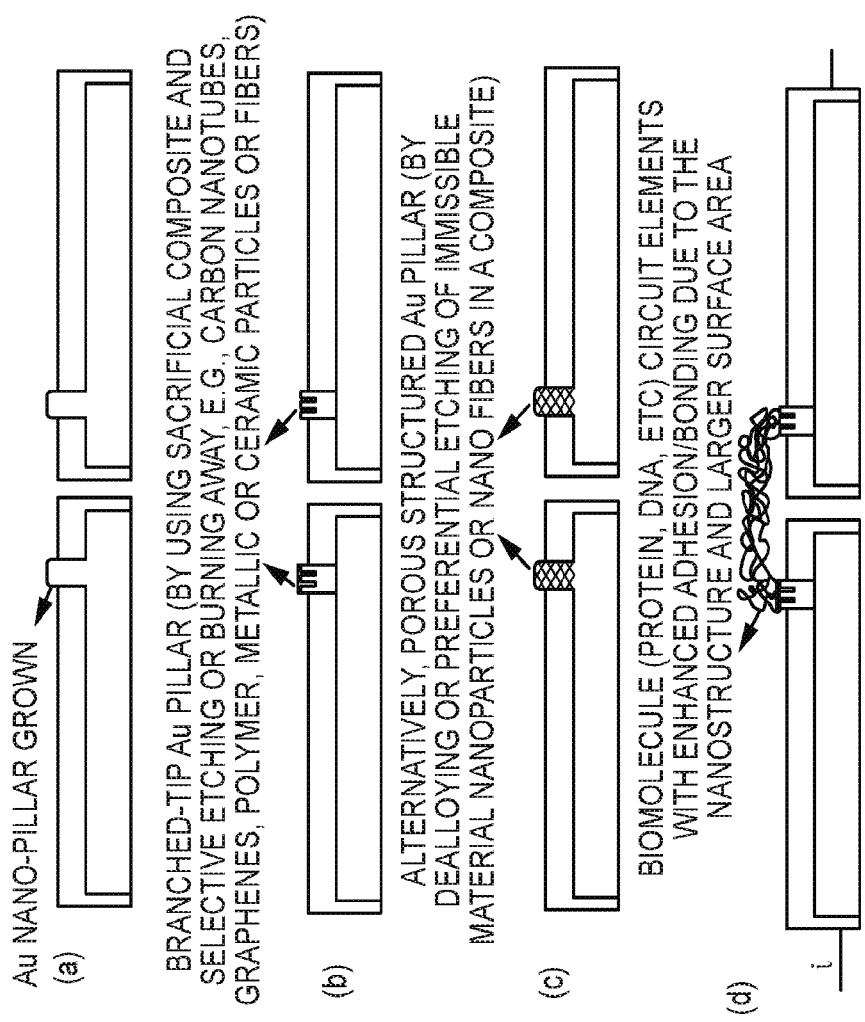
FIG. 5(a) illustrates an exemplary substrate surface with Au pillar structure.
FIGS. 5(b)-(c) illustrate nanostructures of branched and porous Au pillars with enhanced adhesion of biomolecules.
FIG. 5(d) illustrates an exemplary device with biomolecule attached to the Au pillars on the electrodes.

In DNA sequencing and genome sequencing using label-free electronic detection, as well as molecular electronics devices in general, strong and reliable attachment of biomolecules is essential so as to obtain strong signals in a reproducible, noise-reduced manner. An attachment of biomolecules in sensor devices can be enhanced if the surface of the substrate on to which the biomolecule is to bind is modified to exhibit significantly larger surface area. It is difficult to make further branched or porous structures on what are already nano-dimensioned (e.g., 5-10 nm area) structures. However, in accordance with the present disclosure, such difficulty has been overcome. As illustrated in the two examples of FIGS. 5(b) and 5(c), further subdivided nanostructures for enhanced adhesion of biomolecules are possible on Au pillars (e.g. as exemplified in FIG. 5(a)) or on some other nano-dimensioned surfaces. In FIGS. 5(b) and 5(c), branched and porous Au deposits, respectively, provide more powerful and enhanced biomolecule or linker molecule adhesion to the Au contact.

Branched-tip Au pillars, as shown in FIG. 5(b) can be obtained by using sacrificial materials in an Au composite, and selective etching or burning away of about 1%, 3%, 5%, 8%, 10%, 12%, 14%, 16%, 18%, or 20% volume of the non-Au material. In other aspects, from about 5% to about 20% by volume of the non-Au material is selectively etched away or burned away from the Au composite. Sacrificial materials include, but are not limited to, carbon nanotubes, graphene, polymer, or metallic or ceramic phase nanoparticles added during electrodeposition. Alternatively, branched-tip Au pillars may be formed by standard deposition of Au (without electrical current) and then dispersing nanoparticles which are trapped therein to form a composite material. Metallic nanoparticles such as Co, Ni, Fe, Cu, Zn, Al, Si, Mo, V, or ceramic nanoparticles such as CoO or $Co_2O_3$, NiO, $Fe_2O_3$ or $Fe_3O_4$, CuO, ZnO, $Al_2O_3$, $MoO_2$, $V_2O_5$, $SiO_2$ can then be etched away using strong acid (but not as strong as gold etchant like aqua regia solution having nitric acid and hydrochloric acid in 1:3 ratio). The etchant can be a dilute acid or an alkali (e.g. in the case of aluminum particles to be etched away), with the concentration of less than one-half of the acid component used in aqua regia solution, and preferably less than one-quarter of the acid component used in aqua regia solution. When these metals and ceramics are etched away, the remaining Au exhibits a greater surface area comprising a branched or porous nanostructure surface, which is desirable for a stronger binding of biomolecules thereon, including biomolecules such as proteins or DNA. The desirable dimension of metallic, ceramic or polymer sacrificial nanoparticles is less than 10 nm, preferably less than 5 nm, even more preferably less than 2 nm in average diameter. The desirable dimension of sacrificial carbon nanotubes or graphene nano-flakes to be incorporated into the Au composite is less than 8 nm, preferably less than 3 nm, even more preferably less than 1 nm in thickness. Carbon nanotubes, graphene nano-flakes, or polymer nanoparticles in the Au composite matrix can be burned away by heating to a temperature of about 200 to about 500° C., or by dissolving away in a solvent, such as in the case of polymer nanoparticles.

An alternative method of providing porous Au pillars is disclosed in FIG. 5(c). Au pillars or Au nano-islands can be made porous by using a de-alloying method, which in this case, comprises first depositing Au pillars or islands containing alloy components, e.g., Au—Ag, Au—Cu or other Au-based alloys that can be electroplated or electroless plated. The nano-pillars comprising the alloy are then chemically or electrochemically etched in a strong acid (or alkali in the case of Al or Mg type alloying) to selectively remove the non-Au metal(s) from the alloy and leave behind the Au. The desired amount of alloying of Au with Ag, Cu, and/or other metallic elements, is in the range of about 10 to about 70% volume, and preferably in the range of about 30% to about 60% volume. Either an element capable of alloying, or an immiscible element not capable of forming an alloy can be added to Au and then the step of de-alloying or preferential etching will result in a nanostructured Au. The desired % volume of porosity in an Au tip, Au pillar or Au island thus formed is at least at least 10%, at least 20%, at least 30%, at least 40%, or preferably at least 50%. The increase in surface area in the structures illustrated in FIGS. 5(b) and 5(c) achieved by the nanocomposite route is at least by 3%, at least 5%, at least 10%, at least 20%, at least 30%, at least 40%, at least 50%, or at least 60%, over the porosity of a Au tip, Au pillar or Au island as obtained from Au electrodeposition and no modification.

Another embodiment of Au pillar modification is to apply nanoscale sand blasting, masked chemical etching, ion implantation, or other suitable method to intentionally damage the surface of the Au pillar to make it rough and/or porous. In these instances of binding to surface damaged and/or and porous Au, the adhesion strength of the biomolecules is improved by a factor of at least 10%, at least 20%, at least 25%, at least 35%, at least 40%, at least 50%, at least 60%, or at least 70% over the adhesion of the biomolecule to an unmodified Au pillar structure.

In other embodiments, Au pillars may be dimensionally changed by annealing. For example, Au pillars can be converted from relatively cylindrical pillar shapes to spherical-ball shapes by annealing at elevated temperatures, such as temperatures higher than the melting temperature of Au but lower than temperatures at which other components of the device (e.g. the electrodes) may melt or otherwise be damaged.

FIG. 5(d) illustrates an exemplary device wherein a biomolecule (e.g. protein, DNA, or other biomolecule) is attached to the Au portions of the electrodes having the enhanced adhesion/bonding due to the nanostructure and larger surface area present in the Au pillars of FIGS. 5(b) and 5(c). Thus, in the manufacturing of a device comprising electrode pairs, a biomolecule is attached to the contact points on each one of the electrodes in a pair of electrodes in order to bridge the nanogap between the two electrodes in the pair. As discussed above, these contact points may comprise Au nano-pillars, optionally modified by alloying/de-alloying or other methods to increase the surface area and binding capabilities of each nano-pillar.

Figure 3:
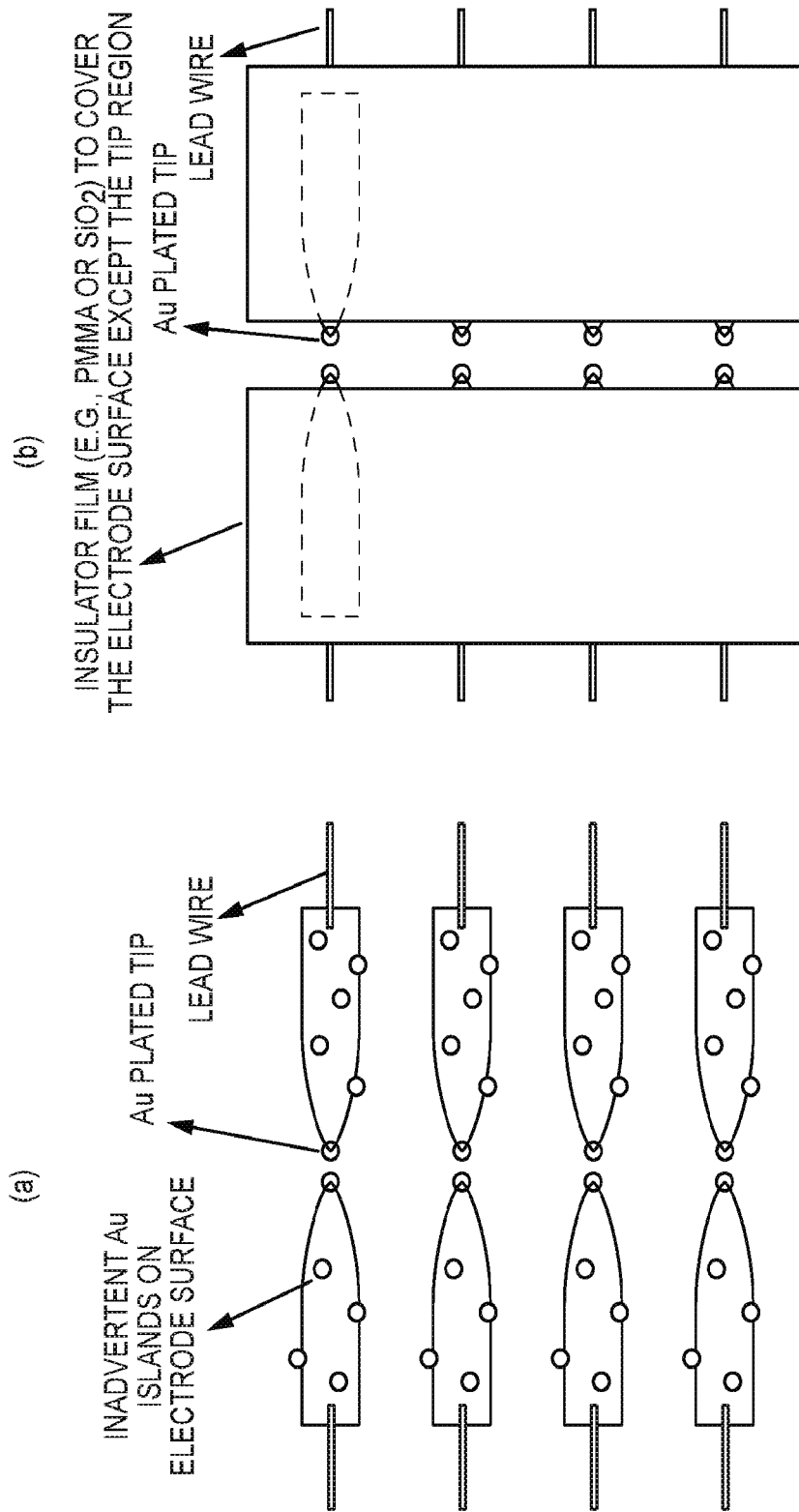
FIG. 3(a) illustrates an Au-tip plated electrode array (e.g., Pt, Pd or Rh) with inadvertent Au islands on electrode surface. Substrate material such as Si with $SiO_2$ surface insulator is not shown.
FIG. 3(b) illustrates a structure that masks the inadvertent Au island deposition to eliminate unwanted biomolecule attachments on an electrode surface.

It should be noted that these new methods to increase the surface area and enhance biomolecule bonding are also applicable for other embodiments, such as those exemplified in FIGS. 2 and 3 and discussed above.

Figure 6:
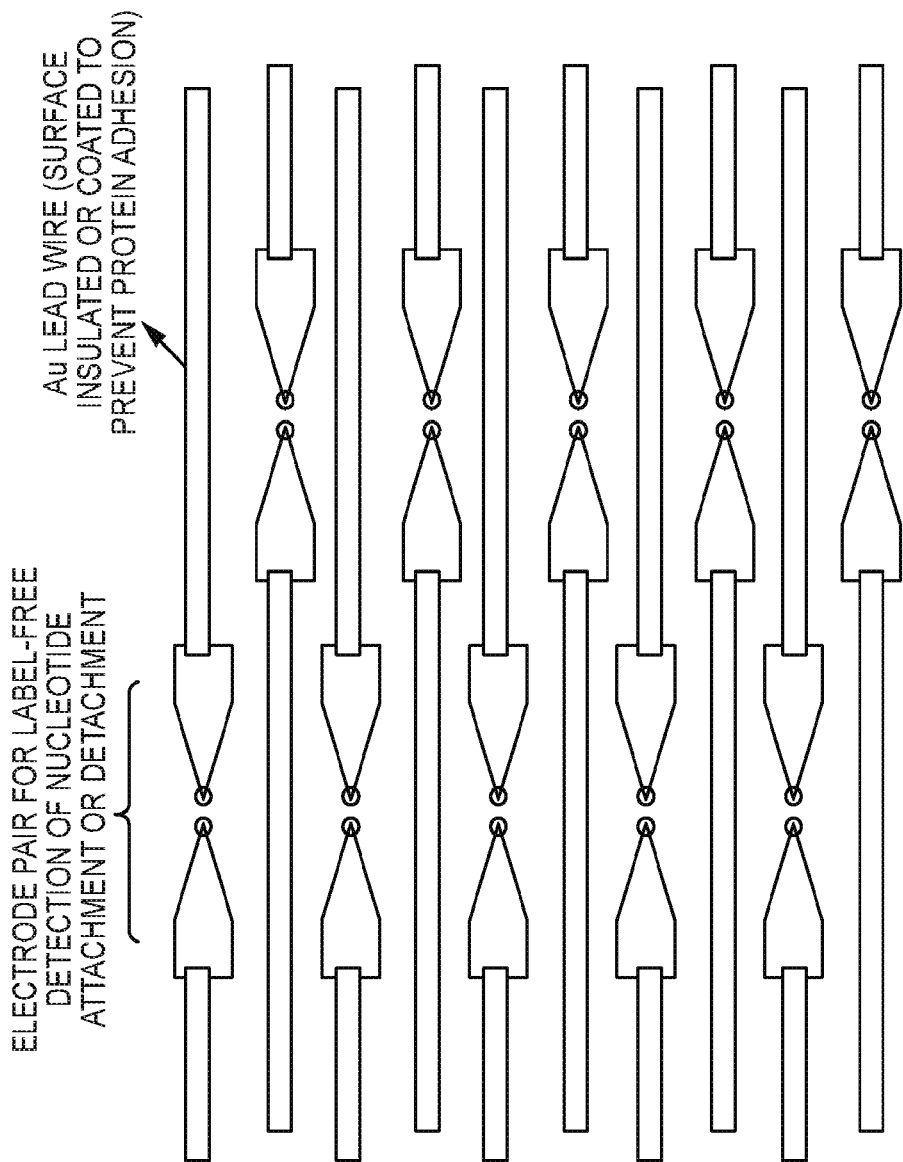
FIG. 6 illustrates an array of Au nano-tip electrode pairs for massively parallel, label-free detection of nucleotide attachment or detachment events (e.g., 100×100 device array or 1,000×1,000 array)

In various aspects of the present disclosure, massively parallel electrode arrays can be produced, with arrays having at least 1,000, preferably at least 10,000, and even more preferably at least 1 million electrode pair devices in the device array. FIG. 6 illustrates an exemplary array of Au nano-tip structured electrode pairs usable for massively parallel, label-free detection of nucleotide or other molecular attachment or detachment events. Such arrays may comprise 100×100 devices or 1,000×1,000 devices, or the like, each device comprising an electrode pair with sharp tipped electrodes (comprising, for example Pt, Pd or Rh), Au nano-tip electrodeposited or electroless deposited at or near the electrode tip area, and Au or other conductor lead wires (e.g., Ag, Cu, Pt, Pd, Rh). If an Au lead wire is used, the surface of the Au leads can be covered with a mask such as PMMA to prevent undesirable biomolecules adhesion on the leads.

Figure 7:
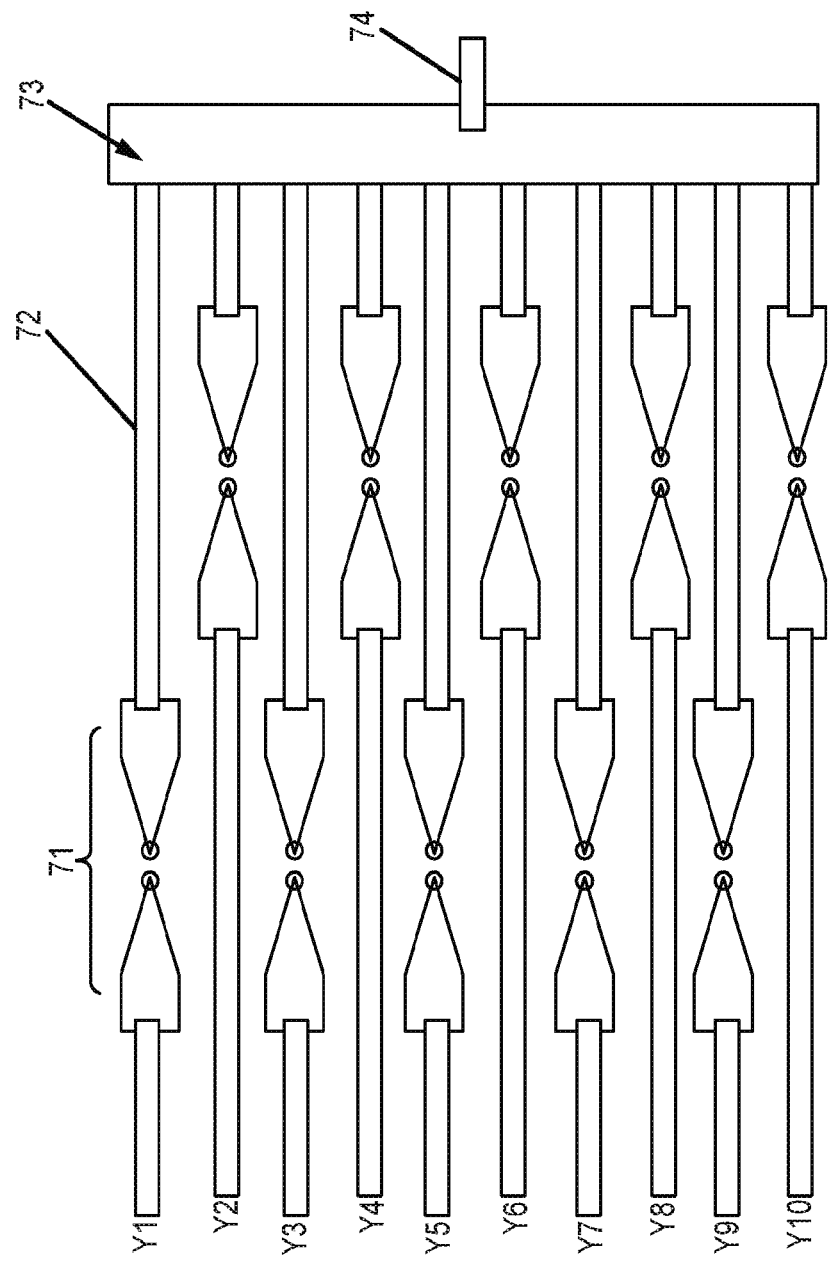
FIG. 7 illustrates sequential interrogation of electrodes by using a common lead wire on one side of the array.

With an array such as the embodiment illustrated in FIG. 6, the interrogation of nucleotide attachment can be performed in real time. An alternative embodiment of electronic signal interrogation is to perform sequential integration by shorting one side of all lead wires and taking turns with left side electrical lead wires one at a time, e.g., every millisecond, such as in the configuration shown in FIG. 7. In FIG. 7, 71 is an exemplary electrode pair for label-free detection of nucleotide attachment or detachment, (wherein the electrode pair would further include a biomolecule bridging the gap and probe molecule), and 72 is an embodiment of a lead wire, such as an Au lead wire, which can be surface insulated or coated to prevent protein or other biomolecule adhesion thereon. With continued reference to FIG. 7, element 73 is a common connection lead wire connecting all of the right side electrodes, and element 74 is just the one common lead wire needed on the right side of the array. The left side electrodes, Y1, Y2 . . . Y10, are interrogated one at a time, sequentially. This wiring configuration and sequential interrogation method results in fewer electronic measurement complications compared to the handling of many thousands of parallel signals all at once.

Figure 8:
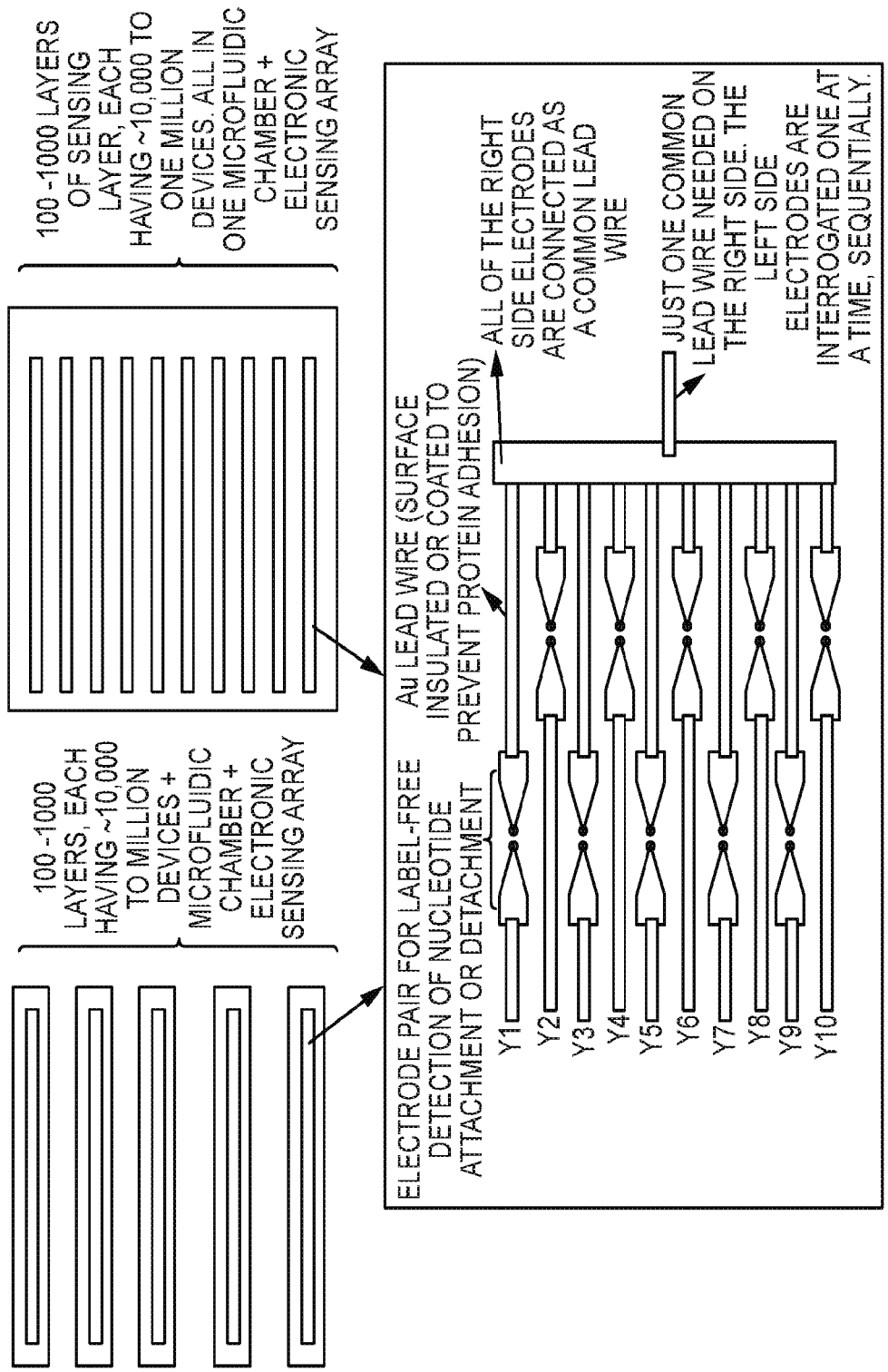
FIG. 8 illustrates a three-dimensional array of molecular electronics genome-sequencing platform.

Even larger data acquisitions can be obtained if the FIG. 6 or FIG. 7 type nano-tip or nano-pillar structure is stacked in three dimensions, such as shown in FIG. 8, with an accompanying microfluidic chamber for each stack (top left in the figure), or with one or more common microfluidic chambers (top right in the figure). In such 3D configurations, at least about one million to about one billion devices can be operated simultaneously for extremely rapid DNA or genome sequencing. In other embodiments, a more sophisticated, micro-wire or micro-ribbon array with protruding Au pillar arrays are used for even higher density biomolecule sensing.

Figure 9:
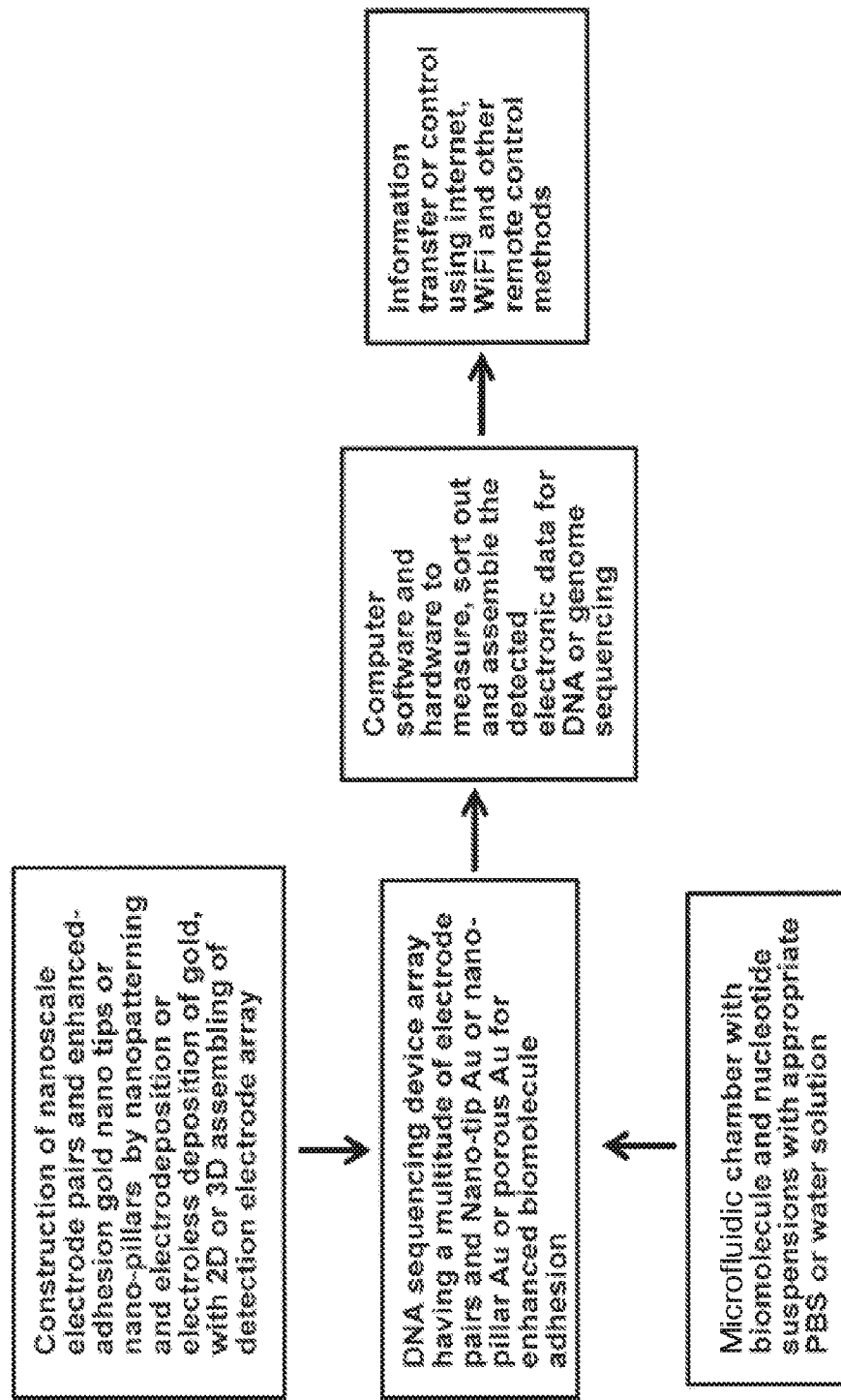
FIG. 9 illustrates a genome or DNA sequencing system according to the invention, comprising a nano-electrode system and biomolecular components properly attached to said electrode using specific contacts and material binding properties.

Aspects of the genome or DNA sequencing structures, systems and methods according to the invention are summarized in FIG. 9. Appropriate software and a computer system are incorporated, and a microfluidic system is connected to the massively parallel electronic detection system. Biomolecules and coupling agents are delivered into the microfluidic chamber(s), together with nucleotides to be sequenced.

Figure 10:
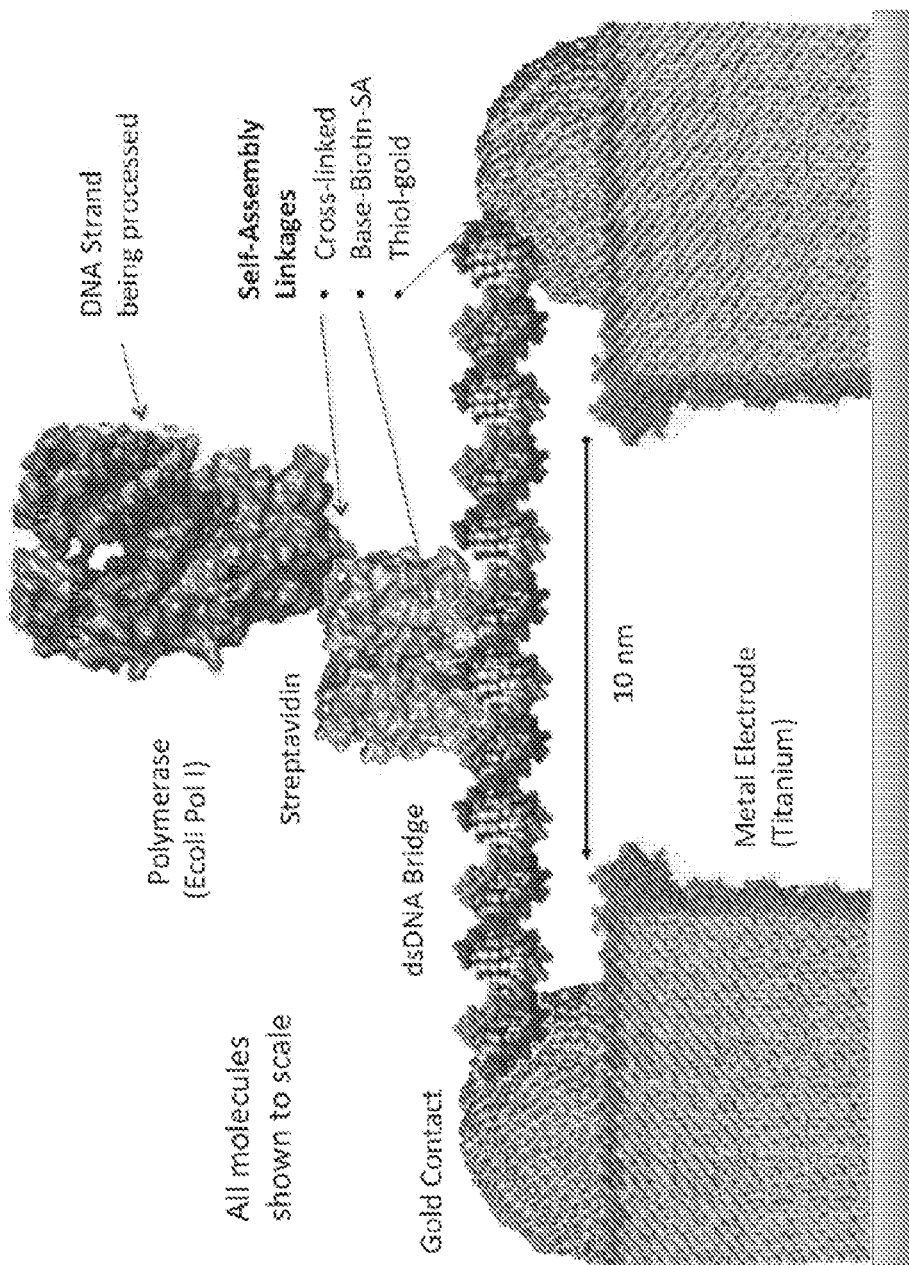
FIG. 10 illustrates a molecular structure used for experimental work on DNA sequence analysis, comprising a bridge and probe molecule.

FIG. 10 illustrates an embodiment of a molecular structure used for DNA sequence analysis, comprising a bridge and probe molecule structure. In this illustrated example, the bridge biomolecule comprises a synthetic double stranded DNA oligo molecule, 20 nm in length (60 bases), with thiol groups at both 5' ends of the molecule for coupling to the Au contact points provided on the metal electrodes. In this way, one bridge biomolecule bridges the ~10 nm nano-gap between the electrodes in each electrode pair. The Au contact points of each electrode pair may comprise any of the Au structures discussed herein above, such as, for example, Au dots electrodeposited on sharp ends of the electrodes or Au pillars grown by electrodeposition of Au into unmasked areas near the tips of the electrodes, and so forth. The metal electrodes may comprise platinum (Pt), palladium (Pd), rhodium (Rh) or gold (Au). In the latter case of Au, the contact points and the electrodes comprise an integration of the same metal, i.e. Au. With continued reference to FIG. 10, the probe molecule comprises a polymerase, for example, *E. coli* Pol I, which is chemically crosslinked to a streptavidin protein, which in turn is coupled to the bridge molecule at a biotinylated nucleotide provided within the synthetic DNA oligo sequence. The figure is shown to scale in regard to the sizes of the molecules and atoms.

Figure 11:
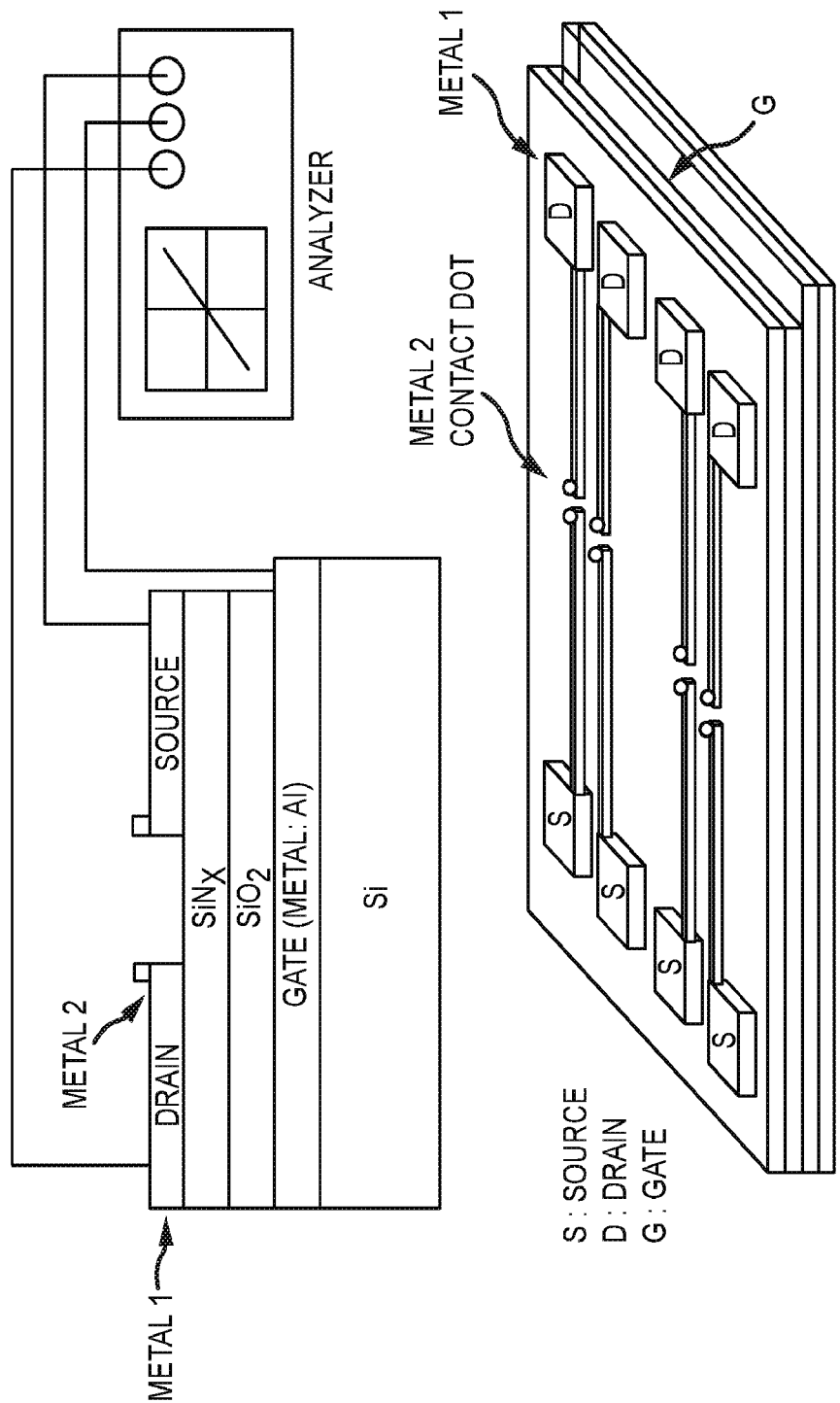
FIG. 11 illustrates an exemplary test set-up for electrical measurements on molecular sensors. The structure at top is a cross sectional illustration of an electrode-substrate structure, and attachment to analyzer for applying voltages and measuring currents through the bridge molecule. The structure at bottom is a perspective view of electrode array for bridging circuits.

FIG. 11 illustrates an exemplary test set-up usable for electrical measurements on molecular sensors. Illustrated at top is a cross-sectional depiction of an electrode-substrate structure, and attachment to an analyzer for applying voltages and measuring currents through the bridge molecule. The structure at bottom is a perspective view of an electrode array for bridging circuits. Each pair of electrodes is illustrated as comprising Metal-2 contact points on Metal-1 electrodes. As discussed above, the Metal-1 electrodes may comprise Pt, Pd, Rh, or Au, and the Metal-2 contacts points comprise Au. In various embodiments, Metal-1 and Metal-2 are both Au, such as when Au pillars are grown on unmasked areas of Au electrodes. In the present example, the Au tips or pillars support self-assembly of thiolated molecules in place by capitalizing on the strong thiol-Au binding.

Figure 12A:
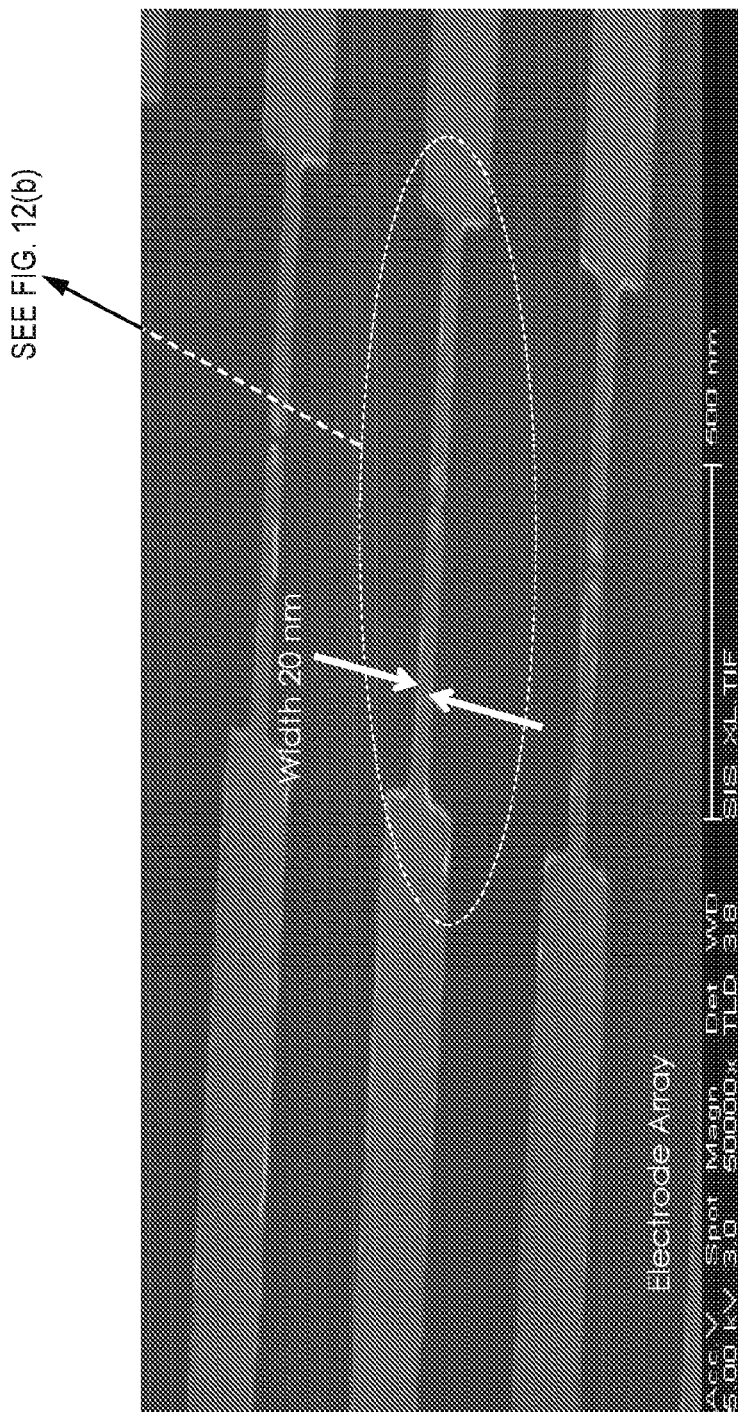
FIG. 12(a) provides an electron microscope image of electrodes with gold metal dot contacts for bridge binding. Electrodes are on a silicon substrate, produced via e-beam lithography. The image is of an array of titanium electrodes with gold dot contacts.
Figure 12B:
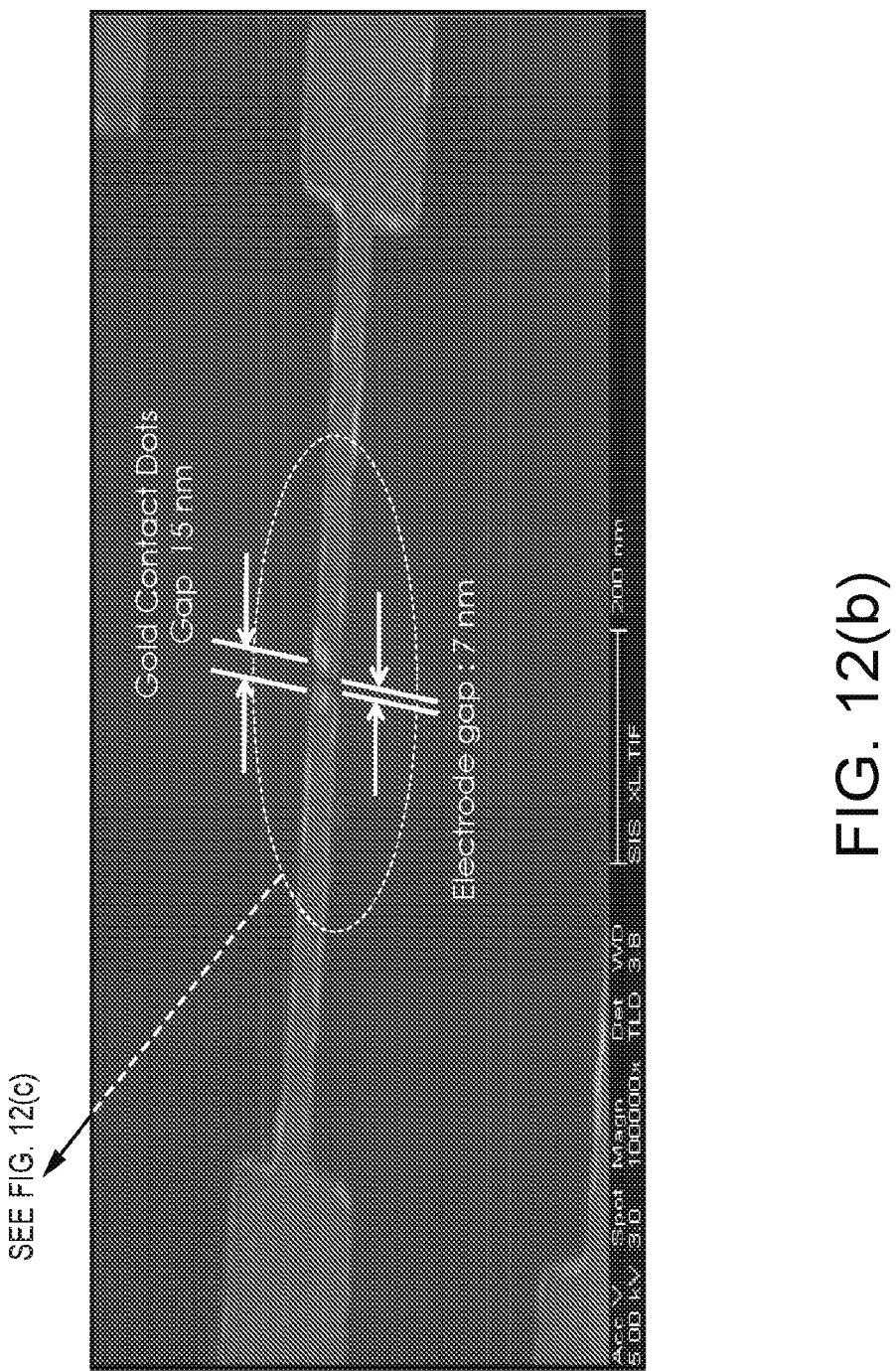
FIG. 12(b) provides an electron microscope image of electrodes with gold metal dot contacts for bridge binding. Electrodes are on a silicon substrate, produced via e-beam lithography. The image is a close-up of the array in FIG. 12(a), showing an electrode gap of 7 nm with gold dot contacts having 15 nm gold-to-gold spacing.
Figure 12C:
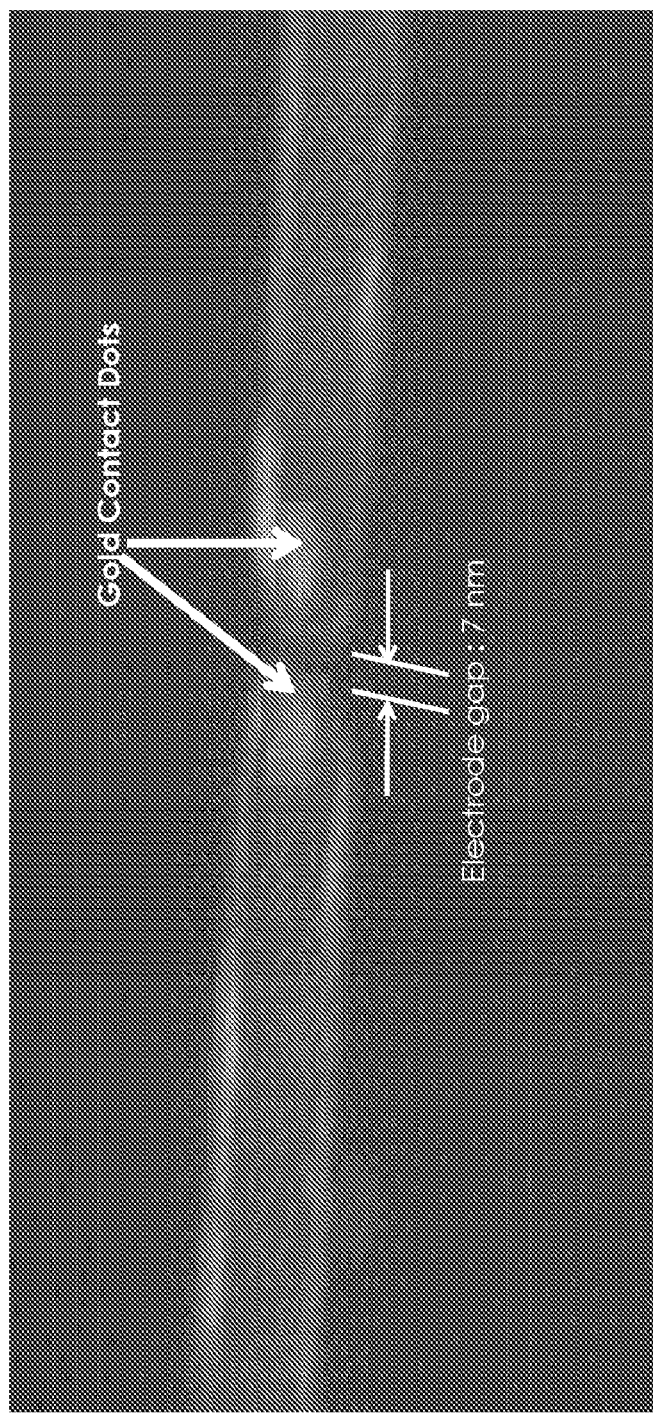
FIG. 12(*c*) provides an electron microscope image of electrodes with gold metal dot contacts for bridge binding. Electrodes are on a silicon substrate, produced via e-beam lithography. The image is a close-up of the array in FIG. 12(*b*), showing approximately 10 nm gold dots at the tips of the electrodes.

FIGS. 12(*a*)-(*c*) set forth electron micrographs of successfully constructed electrode pairs comprising Au contact points. FIG. 12(*a*) is an electron microscope image of Ti electrodes comprising Au dot contacts for bridge molecule binding. In this example, the Au dots were electrodeposited at or near the ends of the Ti electrodes. Electrodes are disposed on a silicon substrate, produced via e-beam lithography. FIG. 12(*b*) is an electron micrograph at higher resolution. The image is a close-up of the array in FIG. 12(*a*), showing an electrode gap of 7 nm with Au dot contacts having 15 nm Au-to-Au spacing. FIG. 12(*c*) is an electron micrograph at even higher resolution. The image is a close-up of the array in FIG. 12(*b*), showing approximately 10 nm Au dots deposited at the tips of the electrodes.

Figure 13:
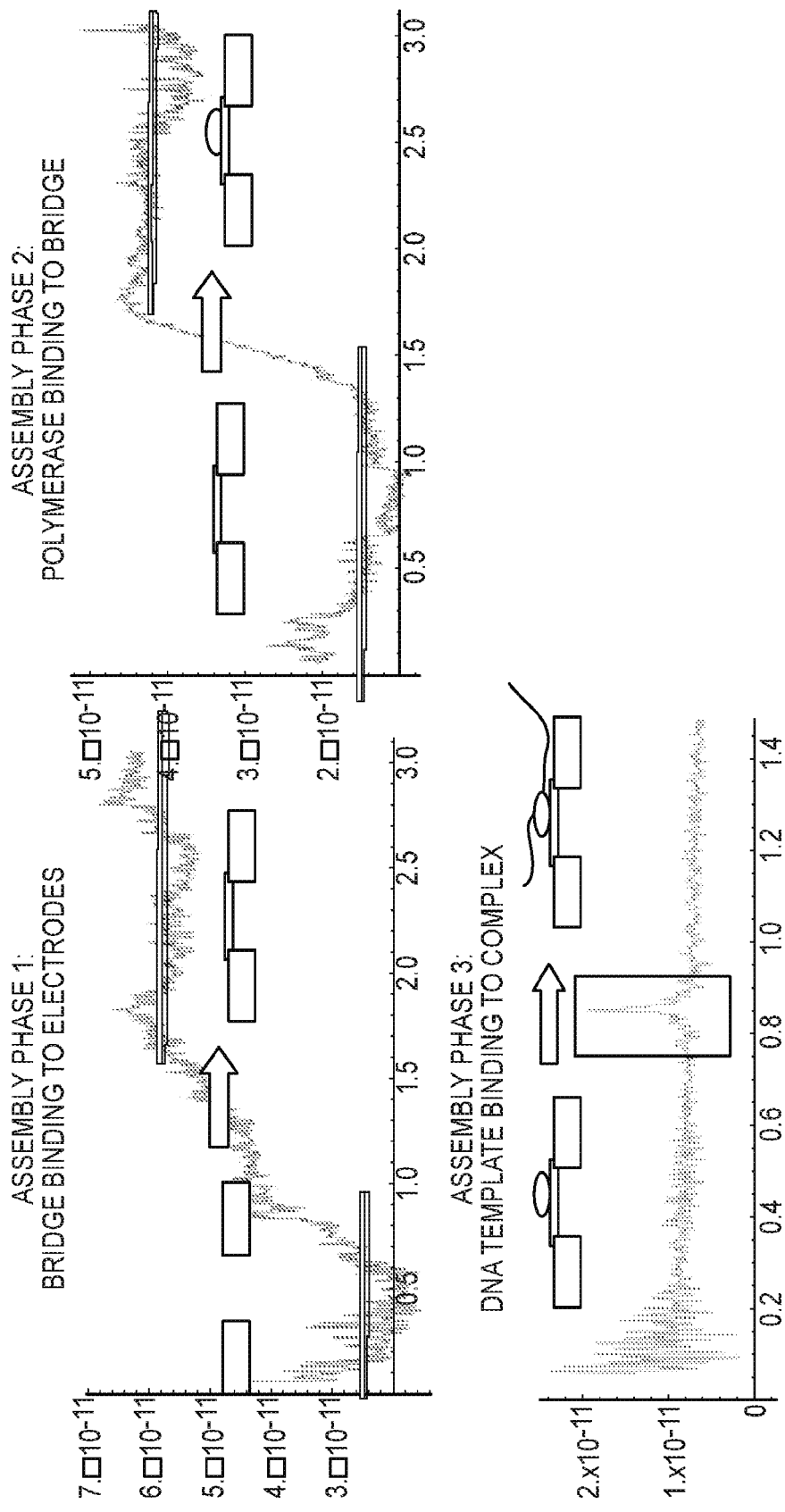
FIG. 13 illustrates electronic monitoring of the various phases of molecular sensor self-assembly onto gold-dot contact electrodes.

With reference now to FIG. 13, the process of molecular sensor self-assembly onto gold-dot contact electrodes is shown being electronically monitored. Current versus time measurements are used to monitor self-assembly of the bridge and molecular sensor complex. The plot at the upper left shows Phase 1 of the self-assembly, wherein a double stranded DNA bridge with thiol groups on the 5' ends assembles onto electrode gold contact point, as evidenced by a jump in current. The plot at the upper right shows Phase 2 of the self-assembly process, wherein polymerase-streptavidin complex binds to a biotinylated site on the dsDNA bridge, as evidenced by another jump up in current. The plot at the lower left shows Phase 3 of the self-assembly process, wherein a primed single-stranded DNA template binds to the polymerase to complete the complex, as evidenced by another spike in current versus time.

Figure 14:
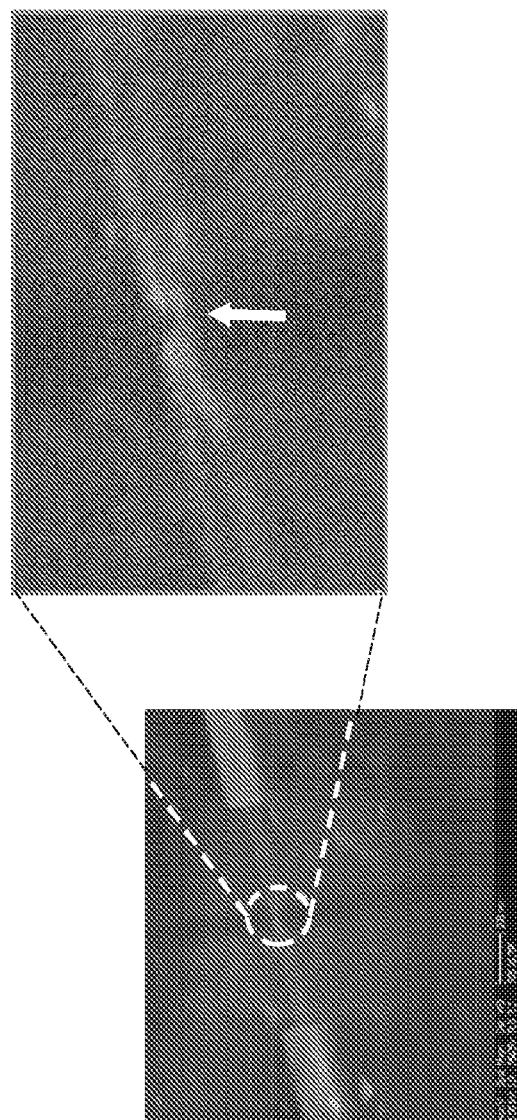
FIG. 14 provides EM imaging of the final self-assembled structure upon completion of the phases depicted and monitored in FIG. 13.

FIG. 14 provides electron microscope imaging of the final self-assembled structure upon completion of the self-assembly phases depicted and monitored in FIG. 13 and discussed herein. In this electron micrograph, the bridge-complex is directly visible without labeling, and can be seen as a slightly blurry higher contrast region joining the electrode pair (and indicated by the white arrow in the higher magnification image at the right). In the lower magnification image at the left, the narrower portions of the two electrodes in the pair have a width of about 20 nm and a nanogap between the electrodes of about 7 nm. The image at left focuses on one pair of electrodes out of an array of pairs of electrodes. The whitish portions at the tips of each electrode, seen in both the lower magnification image at left and the higher magnification image at right, are the gold (Au) islands, onto which the biomolecule is bound. As evident in the higher magnification micrograph at the right, the biomolecule, (the whitish higher contrast blur between electrode tips) is seen as contiguous from one tip to the other across the nanogap. Thus, from these micrographs, it is evident that the biomolecule has self-assembled onto each electrode in the pair, with each end of the biomolecule attached to each electrode and forming a bridge across the nanogap.

Figure 15:
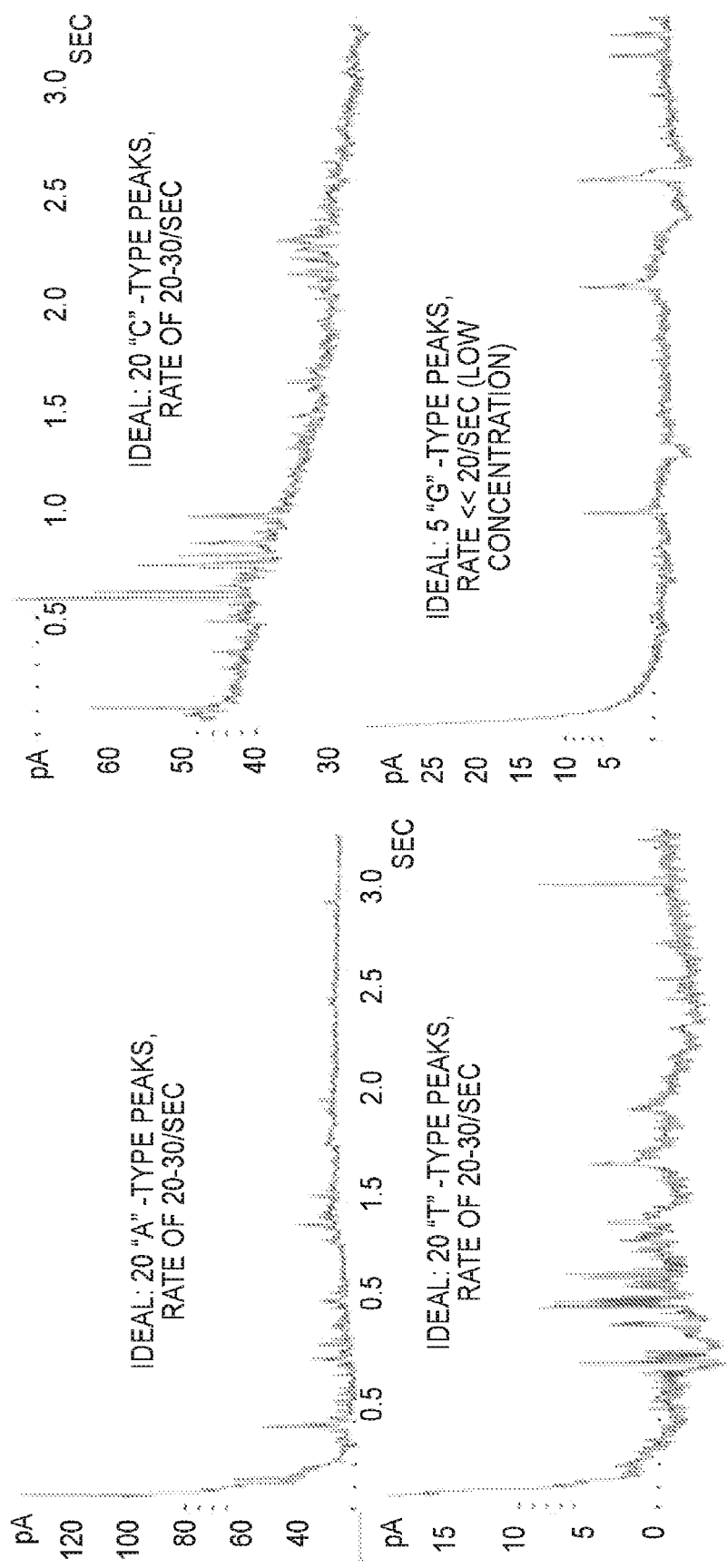
FIG. 15 illustrates the measuring of incorporation signals using an exemplary sensor.

With reference now to FIG. 15, the measuring of incorporation signals using the sensor is demonstrated. The plots in FIG. 15 show the current signals resulting from the sensor being supplied with various primed, single stranded DNA sequencing templates and dNTPs for incorporation and polymerization. In each case, the major signal spikes represent signals resulting from discrete incorporation events, wherein the polymerase enzyme adds another base to the extending strand. In the plot at the upper left, the template is 20 T bases. In the plot at the upper right, the template is 20 G bases. In the plot at the lower left, the template is 20 A bases. Lastly, in the plot at the lower right, the template is 20 C bases. The approximate rate of incorporation observed is about 10 to 20 bases per second, which is consistent with standard enzyme kinetics except for the lower rate of ~1 base per second presumed due to rate limiting factors (e.g., lower dNTP concentration).

Figure 16:
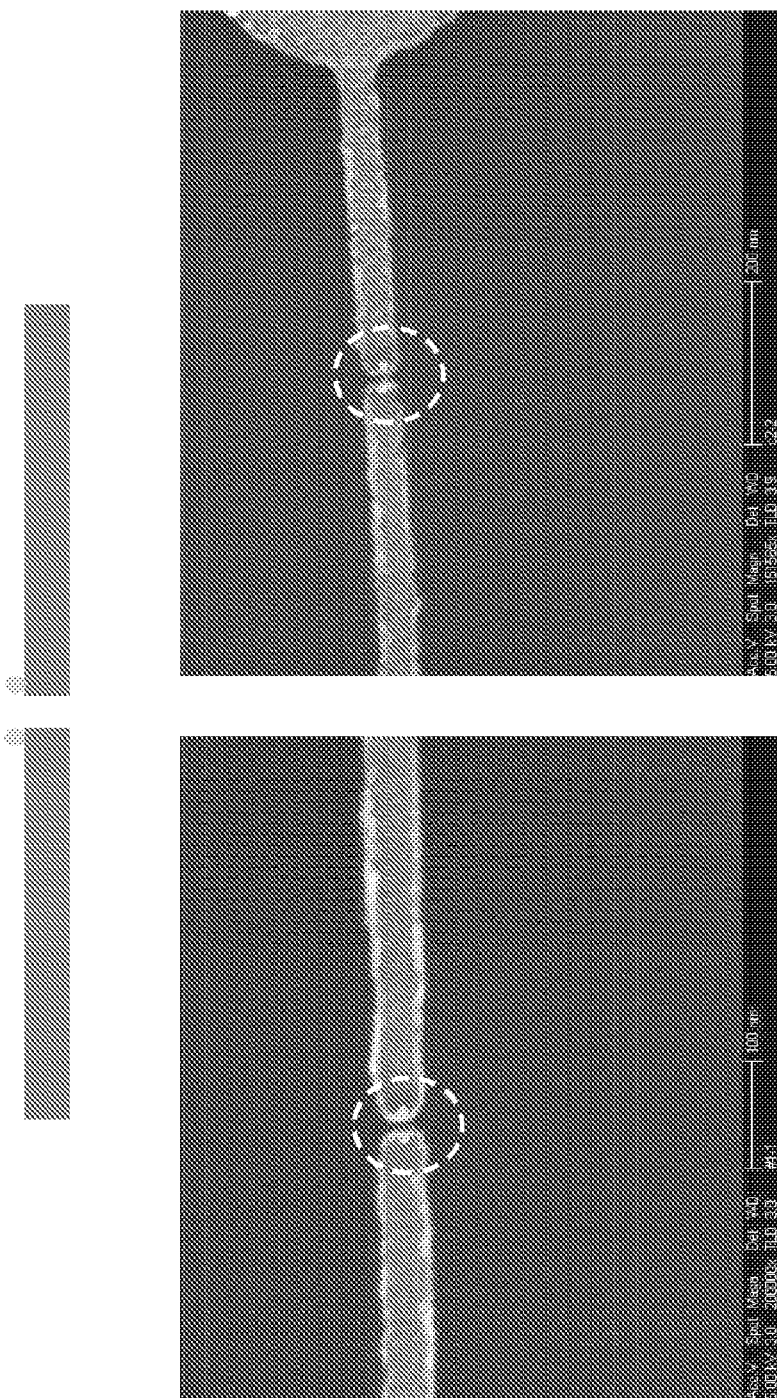
FIG. 16 provides images of fabricated electrodes with Au-dot island contact points.

With reference now to FIG. 16, electron micrograph images are provided that show two separate fabricated electrode pairs, each comprising Au-dot island contact points. The illustration above the micrographs diagrammatically shows how these electrodes and contact points would look like in a side view. As evidenced in the micrographs, these electrode pairs, which are usable for DNA sequencing, have a 5-20 nm nano-gap and a pair of Au islands at the ends of the electrodes for attaching or immobilizing biomolecules, such as proteins or fragmented DNA, which will be bridged one molecule over each nano-gap. Devices comprising electrode pairs with bridging biomolecules are useful in the fluorescence-free (label-free) detection of DNA sequencing via electrical measurements. In the example evidenced as successful in these micrographs, structures were made by a two-step e-beam lithography patterning followed by metal deposition and lift-off process. In this case, Au pillars were deposited on the electrode tips and subsequently converted to spherical-ball Au islands by annealing the electrodes at elevated temperature.

Figure 17:
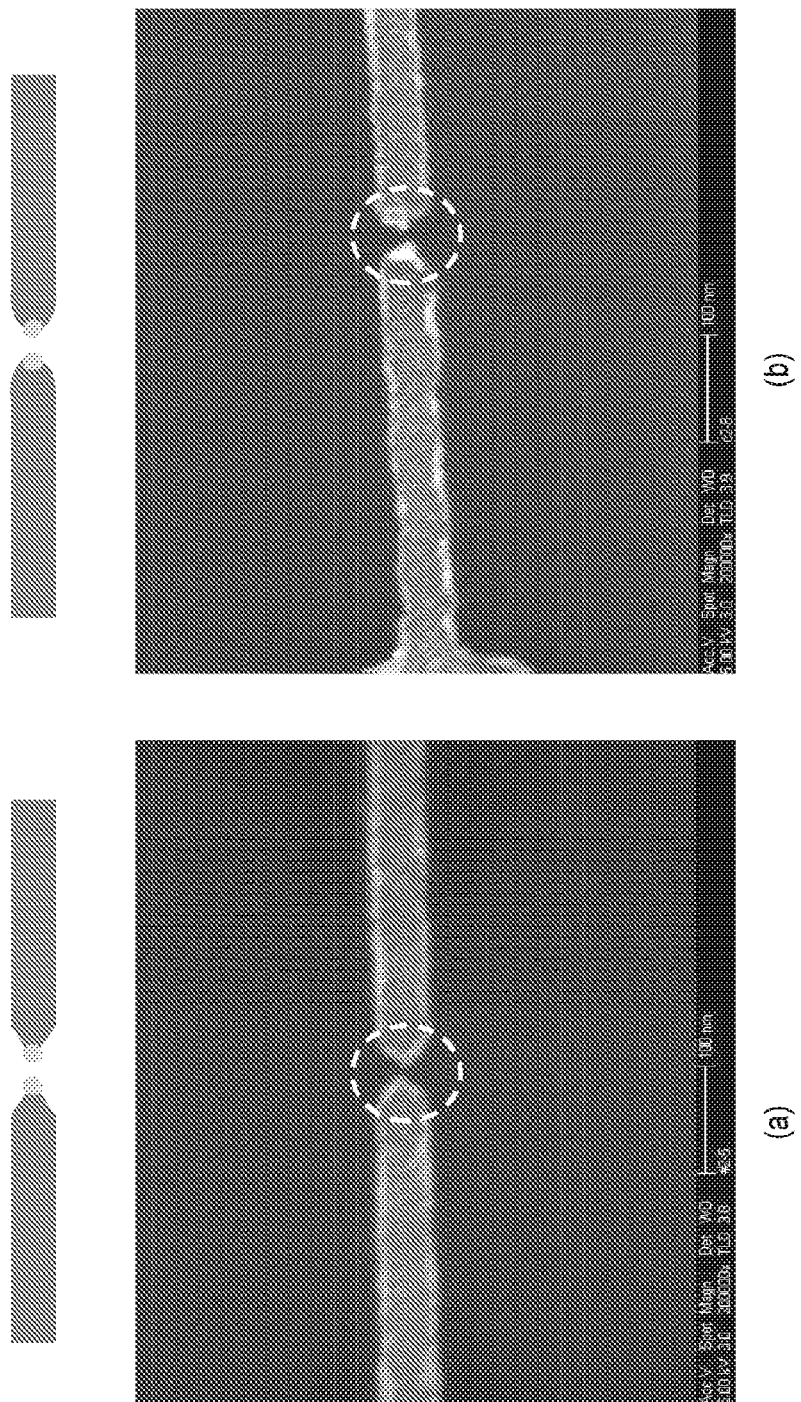
FIG. 17 provides images of fabricated sharp-tip (a) and tapered tip (b) electrodes with Au islands from Au electrodeposition.

FIG. 17 sets forth two embodied electrode pair structures (a) and (b). The illustration at the top of each embodiment is a diagrammatic representation of the electrode structure, and the electron micrograph below shows the successful embodiment. Both (a) and (b) images are top views of nano-electrode geometries with different shapes, each produced by nano-imprint lithography for scaled-up manufacturing or e-beam lithography. In the (a) embodiment, sharp-tip electrodes comprising a pointed end were deposited with Au islands using electrodeposition. In the (b) embodiment, the sharp-tip electrodes are provided with a curvature culminating into narrow portions of the electrode where the Au is preferentially deposited. In the (b) embodiment, the Au islands were also electrodeposited. In both (a) and (b) embodiments, the preference for the Au to deposit at the sharp ends of the electrodes is evident. As discussed above, the sharp ends of the electrodes experience a higher charge density during electrodeposition, and the Au is preferentially deposited at those sites having higher charge density. Although only one pair of electrodes is imaged in the embodiments (a) and (b), massively parallel operations are executed, wherein Au islands are electrodeposited on a plurality of electrodes, localized at the electrode tips by utilizing the sharp or tapered points to induce higher current density for preferential deposition at or near the electrode tips.

Figure 18:
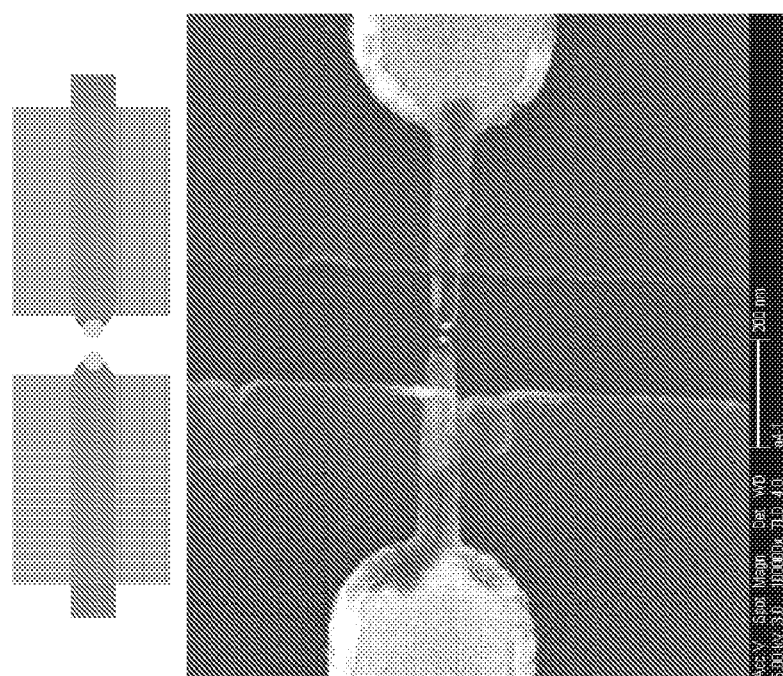
FIG. 18 provides an electron micrograph showing passivation of electrode surfaces to expose only the critical regions of the electrodes for molecular self-assembly binding to gold.

With reference now to FIG. 18, the addition and use of a passivation layer is exemplified. As discussed, Au deposition may occur at sites on the electrodes other than at or near the electrode tips and these errant deposits would be capable of entering into unwanted binding with biomolecules. Thus, in various embodiments, these inadvertent Au deposits can be covered up with passivation such that only the critical regions, i.e. the tips, of the electrodes remain exposed and available to participate self-assembly binding with biomolecules. At the top of FIG. 18, an illustration is provided to show diagrammatically where the passivation layers are located in relation to the electrode pair. The electron micrograph shows the passivation layer successfully in place over the electrode pair. The passivation layer shown in the micrograph, added in this case by e-beam lithography patterning, prevents unwanted biomolecule attachment to any other Au present as errant deposits on the electrode surface.

In addition, such a passivation layer protects the electrodes from chemical exposure to solutions and prevents unwanted leakage current flowing through various solutions. The passivation layer embodied here is $SiO_2$, although a variety of other insulating materials compatible with lithographic methods could be used, such as polymer resists (e.g., PMMA, SU8, etc.), or semiconductor-based materials such as silicon nitride. Also, other nano-lithography patterning can be used to add a passivation layer over the electrodes besides e-beam lithography.

Figure 19:
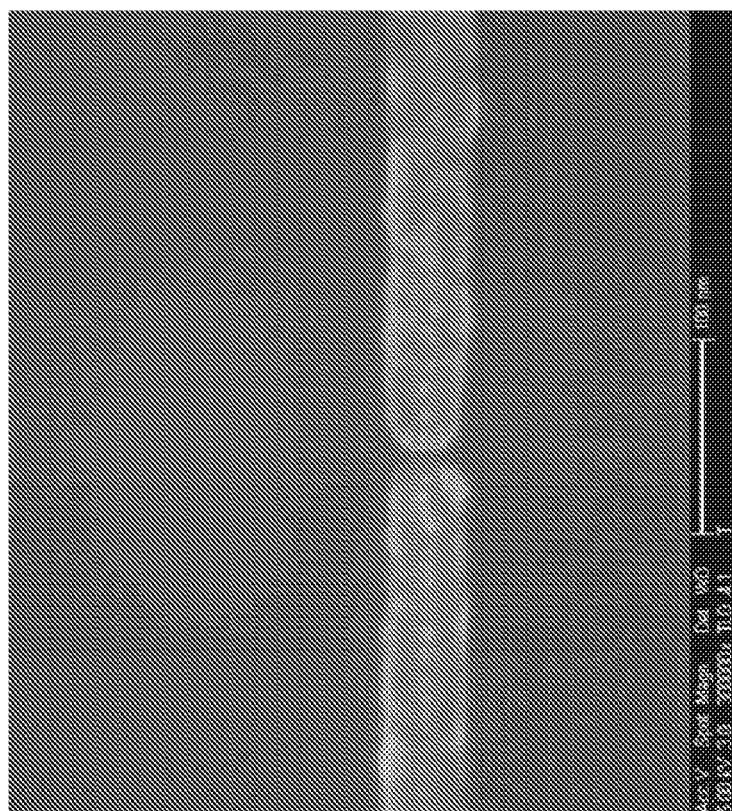
FIG. 19 provides an electron micrograph demonstrating an embodiment of fabricated multi-gold-bead electrodes.

FIG. 19 sets forth an electron micrograph demonstrating fabricated multi-Au-bead electrodes. In this example, a thin gold film was deposited on Ti electrodes and then the deposited film annealed. The results, as evidenced in the micrograph, are rows of uniformly sized and spaced Au beads arrayed along the centerline of the electrodes.

Figure 20:
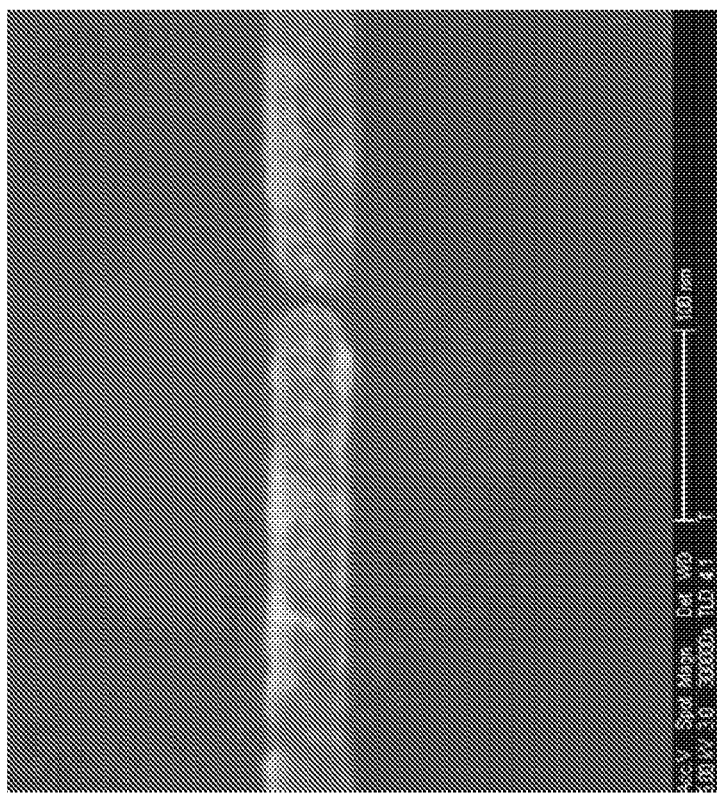
FIG. 20 provides an electron micrograph demonstrating another example of fabricated multi-gold-bead electrodes.

FIG. 20 provides an electron micrograph demonstrating another embodiment of fabricated multi-gold-bead electrodes. This illustrates the result of annealing a thin Au film deposited on an underlying Ti electrode, which produces rows of uniformly sized and spaced Au beads arrayed along the centerline of the electrodes.

Figure 21:
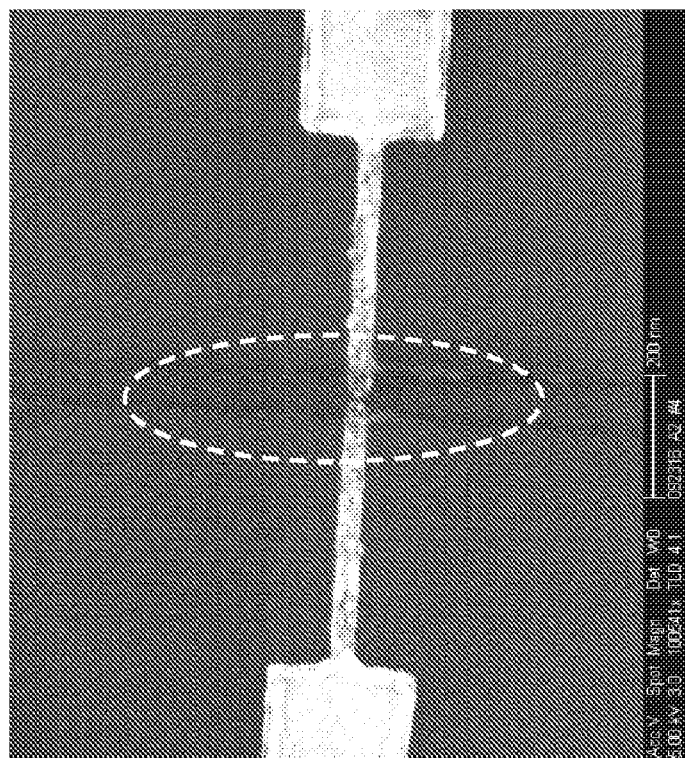
FIG. 21 provides an electron micrograph depicting addition of a passivation layer for use in sensing applications.

FIG. 21 provides an electron micrograph demonstrating successful addition of a passivation layer for use in sensing applications, which leaves open only a region near the tips of the electrodes. In this way, only a pair (or at most a few) of Au beads are left exposed as contact points for targeted molecular bridge binding. In this example, the passivation layer is $SiO_2$, leaving open a 100 nm wide region near the tips (indicated by the dashed circle region).

In various embodiments of the present disclosure, it may be desirable to enhance the probability that a biomolecule will attach onto an Au island pair. For this purpose, the surface of a Au island can be made to be as fresh as possible, such as to ensure easier and thus more likely adhesion/attachment of a biomolecule to an Au island, and to ensure a reliable and robust molecular electronic bridge for genome sequencing. An Au surface may become contaminated with trace amounts of organic or inorganic contaminants. An example of such a contaminant is a carbonaceous coating, occurring when an electrode with Au islands has been left in air or in contact with an aqueous solution or solvent for an extended period of time.

Figure 22:
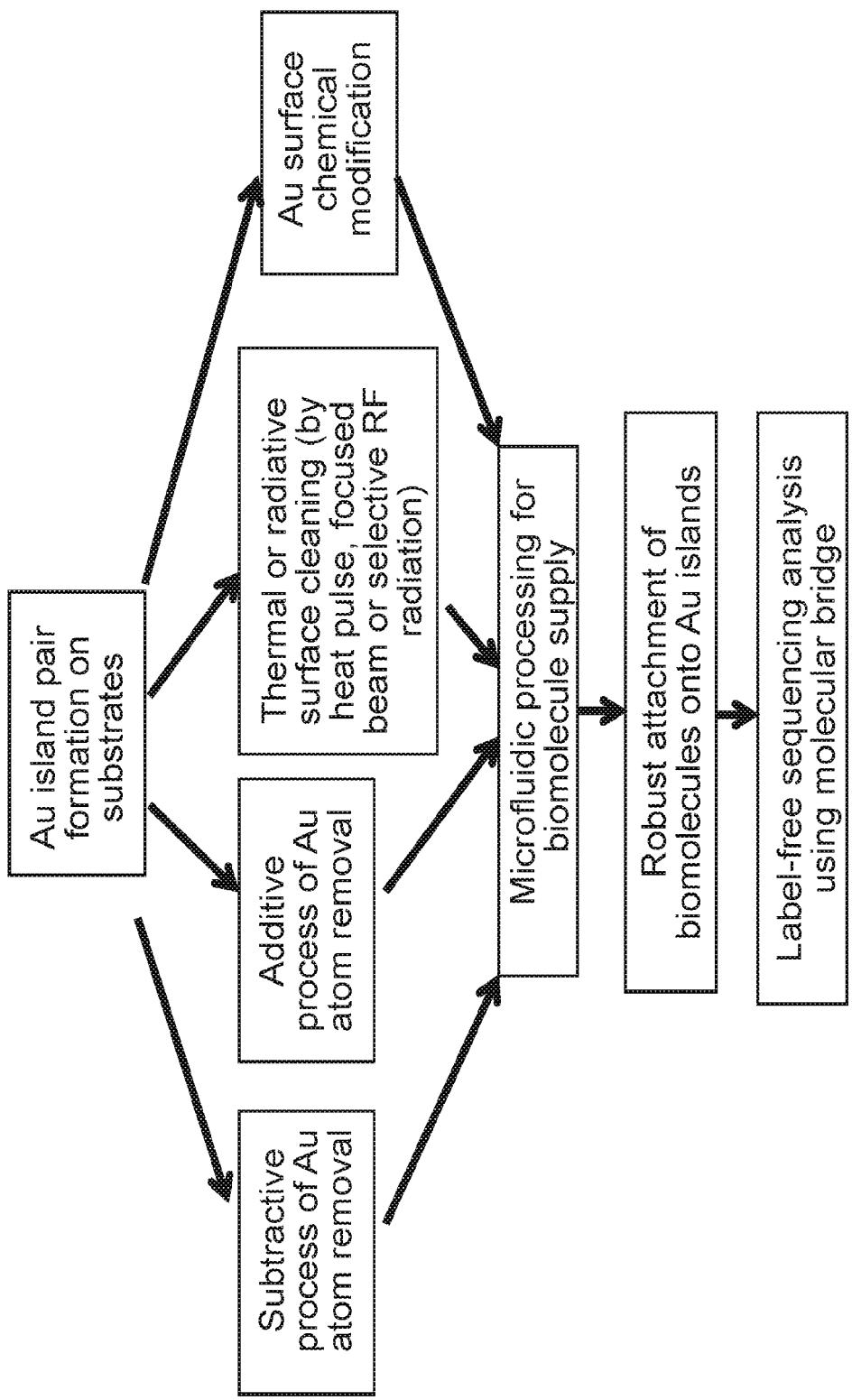
FIG. 22 provides a flow diagram showing various approaches for providing a fresh surface of Au, such as after the step of depositing Au islands.

In accordance with the present disclosure, several novel approaches are used to ensure a fresh Au surface on the Au islands. These approaches include, but are not limited to, (1) a subtractive process; (2) an additive process; (3) a thermal or radiative surface cleaning process; and (4) modification of the Au surface composition. These approaches are explained in detail herein below. FIG. 22 illustrates a flow-chart showing these four different approaches, and where these methods fit in a timing sequence to other steps used to make a label-free sequencing analysis device. As illustrated in the flow diagram, any one or more of these four methods are performed after the Au island formation on the electrode substrates. That is, Au islands would be first deposited onto nano-electrodes, (e.g. Pt, Pd, Rh, Ti, or Au). Then if some errant contamination occurs thereafter, at least one of these approaches can then be used to refresh the Au surfaces of the Au islands. In other embodiments, any one or more of these four processes can also be used on Au nano-electrodes to freshen the surface of the Au nano-electrodes prior to deposition of Au islands. Thereafter, the Au islands deposited on Au nano-electrodes may have developed a contamination, and one or more of the four processes can be repeated again, this time to refresh the surfaces of the Au islands. In either scenario, after the Au islands are freshened by per-forming at least one of these four processes, then the nano-electrode array is encased in a microfluidic environment and subjected to a biomolecule supply, such as an aqueous solution. As indicated in the flow chart of FIG. 22, robust attachment of the biomolecules to the Au islands will occur, due to the fresh Au surfaces on the Au islands. Thereafter, the devices can be used for label-free sequencing analysis by use of the molecular bridges across each nano-electrode pair.

Subtractive Process:

In order to expose a fresh Au surface, the Au island pairs are subjected to sputter etching or ion etching. The amount of Au removed should be minimal so that the removed Au atoms do not end up deposited onto nearby areas whereupon biomolecules may inadvertently attach. In various embodiments, the amount of Au to be removed comprises the equivalent to at most 10 atomic layers of Au on average. In other embodiments, the amount of Au to be removed comprises the equivalent to at most 5 atomic layers of Au. In other embodiments, the amount of Au to be removed comprises the equivalent to at most an average 2 atomic layers of Au.

Additive Process:

A very thin layer of new Au atoms can be added onto the surface of the existing Au islands. Sputter deposition, evaporation, electroless deposition, electroplating, or ion implantation can be performed to add a fresh amount of Au. The amount of newly added Au should be minimal so as not to deposit Au on nearby areas, which may induce unwanted bonding of biomolecules to these nearby regions. In various embodiments, the amount of Au to be added by these or other methods is equivalent to at most 5 atomic layers of Au on average. In other embodiments, the amount of Au to be added is equivalent to at most 3 atomic layers of Au, or at most 1 atomic layer of Au.

Thermal or Radiative Surface Cleaning:

A device structure comprising a pair of Au islands for molecular bridge formation can be subjected to a thermal annealing process, such as by exposing the Au island containing device to a temperature of from about 100° to about 500° C., and preferably from about 200° to about 400° C., for a total time period of from about 0.01 to about 10,000 minutes in air, nitrogen, or argon, or in any other inert atmosphere. The example given below demonstrates the more robust biomolecule attachment to refreshed Au islands.

For electronic sensor devices comprising temperature-sensitive semiconductor components, an exposure to temperatures higher than about 200° C. is not desirable. In such a case, either a short pulse type heating, or a selective localized heating method can be utilized according to the present disclosure. More detailed descriptions for various methods of radiation treatment according to the invention are provided below:

In various embodiments of short-pulse heating (i.e., thermal radiation), a high intensity yet broadened areal beam of infrared (IR) or laser light can be radiated onto a device surface, such as in a pulse mode heating (e.g., more frequent than 10 pulses per minute) so that the heat propagation to the electronic device regions underneath is minimized.

In alternative embodiments, a highly focused laser beam or infrared light beam can be employed so as to locally heat up the regions near the Au islands, e.g., with a beam diameter less that 100 μm, preferably less than 2 μm, and even more preferably less than 0.1 μm. In certain aspects, this can be accomplished by use of a beam focusing wave guide.

In other aspects, selective heating of metallic islands such as Au can be enabled using microwave heating, such as by using repeating pulse mode heating/cool-down cycles. For example, a radio frequency (RF) radiation, e.g., at 5 KHz to 500 KHz frequency, can be utilized, as this RF frequency range tends to preferentially and selectively heat up only conductive components. This is in contrast to microwave radiation in the gigahertz (GHz) range by which metallic as well as non-metallic components, organic/protein materials, and water are all heated up by the radiation.

Au Island Surface Chemical Modifications:

As the Au surface in biological devices may be used in combination with sulfur-containing chemical components (e.g., thiol functionalized chemicals to bond to the Au surfaces), the activity of a Au surface can be enhanced if sulfur atoms are intentionally added. Such modification of Au surfaces with added sulfur atoms can be accomplished in a precisely controlled manner if the sulfur atoms are ion implanted, e.g., at an accelerating voltage of e.g., from about 5 to about 200 KV, and with a dose of about $10^5$ to $10^{16}$ ions/cm$^2$. Implanted ions are lodged into the metal surface where they remain mechanically robust.

Another experimental observation herein is that the type of adhesion layer deposited prior to the Au deposition and subsequent annealing affects how robust the biomolecule attachment is to the Au islands. For example, when the adhesion layer material is a chromium (Cr) film on the substrate surface (e.g., SiO$_2$), rather than a titanium (Ti), zirconium (Zr), or tantalum (Ta) film, the formation and binding performance of Au islands is improved.

After the annealing of Au islands at high temperature (e.g., at 400° C.), some partial diffusional alloying of the Cr or the Ti with the Au in the islands might occur. In this case, Cr, having the greater solid phase solubility with Au, may be beneficial, as it will make the Au islands more semispherical (i.e., less spherical) with enhanced adhesion with a Cr under layer, as compared to using a Ti, Zr, Ta, Hf, or V type adhesion layer of refractory metal elements.

The embodiments described above are only to exemplify the present invention and not to limit the scope of the present invention. Any equivalent modification or variation according to the spirit of the present invention is to be also included within the scope of the present invention.

We claim:

1. A DNA or genome sequencing structure comprising:
   an electrode pair comprising a first metal, each electrode tapering to a tip-shaped end, with the electrodes separated by a nanogap configured to receive a biomolecule; and
   a conductive island of a second metal or metal alloy deposited at or near each tip-shaped end of each electrode wherein the first and second metals are different;
   wherein the biomolecule and the electrode pair form a stationary electronic circuit to detect composition of the biomolecule.

2. The DNA or genome sequencing structure of claim 1, wherein each tip-shaped end comprises a rounded tip configuration.

3. The DNA or genome sequencing structure of claim 1, wherein the nanogap is from about 5 nm to about 20 nm.

4. The DNA or genome sequencing structure of claim 1, wherein the first metal is platinum (Pt), palladium (Pd), rhodium (Rh) or titanium (Ti).

5. The DNA or genome sequencing structure of claim 1, wherein the at least one conductive island deposit comprises a hemispherical nanoparticle.

6. The DNA or genome sequencing structure of claim 5, wherein the second metal is gold (Au).

7. The DNA or genome sequencing structure of claim 1, wherein the at least one conductive island deposit comprises a nanopillar.

8. The DNA or genome sequencing structure of claim 7, wherein the metal alloy is gold-silver (Au—Ag), or gold-copper (Au—Cu) alloy.

9. The DNA or genome sequencing structure of claim 7, wherein the second metal is gold (Au).

10. The DNA or genome sequencing structure of claim 9, wherein the gold (Au) nanopillar further comprises embedded cobalt (Co), nickel (Ni), iron (Fe), copper (Cu), zinc (Zn), aluminum (Al), silicon (Si), molybdenum (MO), or vanadium (V) metallic nanoparticles.

11. The DNA or genome sequencing structure of claim 9, wherein the gold (Au) nanopillar further comprises embedded CoO, $Co_2O_3$, NiO, $Fe_2O_3$, $Fe_3O_4$, CuO, Zn, $Al_2O_3$, $MoO_2$, $V_2O_5$, $SiO_2$ ceramic nanoparticles.

12. The DNA or genome sequencing structure of claim 1, further comprising a biomolecule having two ends, each end of the biomolecule attached to the at least one conductive island deposit on each electrode such that the biomolecule bridges the nanogap, wherein the biomolecule is a protein or a DNA segment.

13. The DNA or genome sequencing structure of claim 12, wherein the protein or DNA segment completes a circuit configured to electronic monitoring of DNA or genome sequencing.

14. A DNA or genome sequencing system, comprising:
   an electrode pair of a first metal disposed on a substrate, each electrode tapering to a tip-shaped end, with the electrodes separated by a nanogap defined by the tip-shaped ends facing one another;
   at least one conductive island deposit of a second metal or metal alloy on each electrode at a location at or near each tip-shaped end of each electrode;
   a biomolecule having two ends, each end of the biomolecule attached to the at least one conductive island deposit on each electrode such that the biomolecule bridges the nanogap; and
   a chamber encasing the electrode pair and defining a microfluidic subsystem configured to supply a solution to the electrode pair;
   wherein the first and second metals are compositionally different.

15. The system of claim 14, wherein the substrate comprises silicon (Si) and an intervening $SiO_2$ insulator layer disposed between the Si substrate and the pair of electrodes.

16. The system of claim 14, wherein the first metal is platinum (Pt), palladium (Pd), rhodium (Rh) or titanium (Ti) and the second metal is gold (Au).

17. The system of claim 14, wherein the nanogap is from about 5 nm to about 20 nm.

18. The system of claim 14, wherein the at least one conductive island deposit comprises a nanopillar.

19. The system of claim 18, wherein the nanopillar is substantially cylindrical, having a diameter of less than about 7 nm and a height of less than about 10 nm.

20. The system of claim 14, wherein the structure comprises a plurality of layers of electrode pairs in a three-dimensional array configuration with electrode pairs connected to one another such that one electrode from each electrode pair is ganged together by a common lead and each of the other electrodes in each pair of electrodes are left unconnected to one another, enabling independent and sequential interrogation of each electrode pair.

* * * * *